(12) United States Patent
Kelter et al.

(10) Patent No.: US 9,265,817 B2
(45) Date of Patent: Feb. 23, 2016

(54) PAT-LM1 EPITOPES AND METHODS FOR USING SAME

(71) Applicant: Patrys Limited, Melbourne, Victoria (AU)

(72) Inventors: Arndt-Rene Kelter, Alfter (DE); Frank Hensel, Wurzburg (DE); Leodevico L. Ilag, Balwyn (AU); Barbara Power, Blackburn (AU); Christopher Garth Hosking, Mount Waverley (AU)

(73) Assignee: Patrys Limited, Melbourne (AU)

( * ) Notice: Subject to any disclaimer, the term of this patent is extended or adjusted under 35 U.S.C. 154(b) by 0 days.

(21) Appl. No.: 14/351,545

(22) PCT Filed: Oct. 29, 2012

(86) PCT No.: PCT/AU2012/001324
§ 371 (c)(1),
(2) Date: Apr. 11, 2014

(87) PCT Pub. No.: WO2013/059886
PCT Pub. Date: May 2, 2013

(65) Prior Publication Data
US 2014/0302074 A1    Oct. 9, 2014

Related U.S. Application Data

(60) Provisional application No. 61/552,794, filed on Oct. 28, 2011.

(51) Int. Cl.
| | | |
|---|---|---|
| C07K 14/00 | (2006.01) |
| A61K 39/00 | (2006.01) |
| G01N 33/574 | (2006.01) |
| C07K 14/47 | (2006.01) |
| C07K 16/30 | (2006.01) |
| C07K 7/06 | (2006.01) |
| C07K 7/08 | (2006.01) |
| C07K 16/18 | (2006.01) |
| A61K 38/00 | (2006.01) |

(52) U.S. Cl.
CPC ............... *A61K 39/0011* (2013.01); *C07K 7/06* (2013.01); *C07K 7/08* (2013.01); *C07K 14/47* (2013.01); *C07K 14/4702* (2013.01); *C07K 14/4748* (2013.01); *C07K 16/18* (2013.01); *C07K 16/30* (2013.01); *G01N 33/574* (2013.01); *A61K 38/00* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 6,159,702 A | 12/2000 | Traish | |
| 6,569,992 B1 | 5/2003 | LaFleur et al. | |
| 7,468,254 B2 * | 12/2008 | Young et al. | ................... 435/7.1 |
| 2005/0063967 A1 | 3/2005 | Young et al. | |
| 2011/0236411 A1 | 9/2011 | Scholler et al. | |

FOREIGN PATENT DOCUMENTS

| | | | |
|---|---|---|---|
| WO | 2004/081027 | | 9/2004 |
| WO | 2009/039854 | * | 4/2009 |
| WO | 2010/004438 | | 1/2010 |

OTHER PUBLICATIONS

Ezzell (J. NIH Res. 1995 7:46).*
Spitler (Cancer Biotherapy, 1995, 10:1-3).*
Boon (Adv. Can. Res. 1992 58:177-210).*
International Search Report for PCT Application No. PCT/AU2012/001324, dated Feb. 1, 2013, 30 pages.
Brundlein, Stephanie, et al. (2002), "Human monoclonal IgM antibodies with apoptotic activity isolated from cancer patients", Human Antibodies, IOS Press, 107-119.

* cited by examiner

*Primary Examiner* — Sheela J Huff
(74) *Attorney, Agent, or Firm* — Carol L. Francis; Bozicevic, Field & Francis LLP

(57) ABSTRACT

The present disclosure relates generally to epitopes of an antibody known as PAT-LM1, and methods for using said epitopes.

5 Claims, 8 Drawing Sheets

```
  1    M  Q  S  N  K  T  F  N  L  E  K  Q  N  H  T  P  R  K  H  H
 21    Q  H  H  H  Q  C  Q  H  H  Q  Q  Q  Q  Q  P  P  P  P  P  P
 41    I  P  A  N  G  C  Q  A  S  S  Q  N  E  G  L  T  I  D  L  K
 61    N  F  R  K  P  G  E  K  T  F  T  Q  R  S  R  L  F  V  G  N
 81    L  P  P  D  I  T  E  E  E  M  R  K  L  F  E  K  Y  G  K  A
101    G  E  V  F  I  H  K  D  K  G  F  G  F  I  R  L  E  T  R  T
121    L  A  E  I  A  K  V  E  L  D  N  M  P  L  R  G  K  Q  L  R
141    V  R  F  A  C  H  S  A  S  L  T  V  R  N  L  P  Q  Y  V  S
161    N  E  L  L  E  E  A  F  S  V  F  G  Q  V  E  R  A  V  V  I
181    V  D  D  R  G  R  P  S  G  K  G  I  V  E  F  S  G  K  P  A
201    A  R  K  A  L  D  R  C  S  E  G  S  F  L  L  T  T  F  P  R
221    P  V  T  V  E  P  M  D  Q  L  D  D  E  E  G  L  P  E  K  L
241    V  I  K  N  Q  C  F  H  K  E  R  E  Q  P  P  R  F  A  Q  P
261    G  S  F  E  Y  E  Y  A  M  R  W  K  A  L  I  E  M  E  K  Q
                                 #178 (Frag1)   ←
281    Q  Q  D  Q  V  D  R  N  I  K | E  A  R  E  K  L  E  M  E  M
                           #179 (Frag2)   ←
301    E  A  A  R  H  E  H  Q  V  M | L  M  R  Q  D  L  M  R  R  Q
                           #180 (Frag3)   ←
321    E  E  L  R  R  M  E  E  L  H | N  Q  E  V  Q  K  R  K  Q  L
                           #181 (Frag4)   ←
341    E  L  R  Q  E  E  E  R  R  R | R  E  E  E  M  R  R  Q  Q  E
                           #182 (Frag5)   ←
361    E  M  M  R  R  Q  Q  E  G  F | K  G  T  F  P  D  A  R  E  Q
                           #183 (Frag6)   ←
381    E  I  R  M  G  Q  M  A  M  G | G  A  M  G  I  N  N  R  G  A
                           #184 (Frag7)   ←
401    M  P  P  A  P  V  P  A  G  T | P  A  P  P  G  P  A  T  M  M
                           #185 (Frag8)   ←
421    P  D  G  T  L  G  L  T  P  P | T  T  E  R  F  G  Q  A  A  T
                           #186 (Frag9)   ←
441    M  E  G  I  G  A  I  G  G  T | P  P  A  F  N  R  A  A  P  G

461    A  E  F  A  P  N  K  R  R  R  Y  *
```

Fragment size                       C-terminal sequence
Frag 1 = 290 aa = 33,1 kD               WKALIEMEKQQQDQVDRNIK
Frag 2 = 310 aa = 35,3 kD               EAREKLEMEMEAARHEHQVM
Frag 3 = 330 aa = 37,6 kD               LMRQDLMRRQEELRRMEELH
Frag 4 = 350 aa = 39,9 kD               NQEVQKRKQLELRQEEERRR
Frag 5 = 370 aa = 42,2 kD               REEEMRRQQEEMMRRQQEGF
Frag 6 = 390 aa = 44,5 kD               KGTFPDAREQEIRMGQMAMG
Frag 7 = 410 aa = 46,7 kD               GAMGINNRGAMPPAPVPAGT
Frag 8 = 430 aa = 49,0 kD               PAPPGPATMMPDGTLGLTPP
Frag 9 = 450 aa = 51,3 kD               TTERFGQAATMEGIGAIGGT
Full   = 471 aa = 53,7 kD               PPAFNRAAPGAEFAPNKRRRY

```
                         SEQUENCE LISTING

<160> NUMBER OF SEQ ID NOS: 67

<210> SEQ ID NO 1
<211> LENGTH: 471
<212> TYPE: PRT
<213> ORGANISM: Homo sapiens

<400> SEQUENCE: 1

Met Gln Ser Asn Lys Thr Phe Asn Leu Glu Lys Gln Asn His Thr Pro
1               5                   10                  15

Arg Lys His His Gln His His His Gln Gln His His Gln Gln Gln
                20                  25                  30

Gln Gln Gln Pro Pro Pro Pro Ile Pro Ala Asn Gly Gln Gln Ala
            35                  40                  45

Ser Ser Gln Asn Glu Gly Leu Thr Ile Asp Leu Lys Asn Phe Arg Lys
    50                  55                  60

Pro Gly Glu Lys Thr Phe Thr Gln Arg Ser Arg Leu Phe Val Gly Asn
65                  70                  75                  80

Leu Pro Pro Asp Ile Thr Glu Glu Met Arg Lys Leu Phe Glu Lys
                85                  90                  95

Tyr Gly Lys Ala Gly Glu Val Phe Ile His Lys Asp Lys Gly Phe Gly
                100                 105                 110

Phe Ile Arg Leu Glu Thr Arg Thr Leu Ala Glu Ile Ala Lys Val Glu
            115                 120                 125

Leu Asp Asn Met Pro Leu Arg Gly Lys Gln Leu Arg Val Arg Phe Ala
130                 135                 140

Cys His Ser Ala Ser Leu Thr Val Arg Asn Leu Pro Gln Tyr Val Ser
145                 150                 155                 160

Asn Glu Leu Leu Glu Glu Ala Phe Ser Val Phe Gly Gln Val Glu Arg
                165                 170                 175

Ala Val Val Ile Val Asp Asp Arg Gly Arg Pro Ser Gly Lys Gly Ile
                180                 185                 190

Val Glu Phe Ser Gly Lys Pro Ala Ala Arg Lys Ala Leu Asp Arg Cys
            195                 200                 205

Ser Glu Gly Ser Phe Leu Leu Thr Thr Phe Pro Arg Pro Val Thr Val
    210                 215                 220

Glu Pro Met Asp Gln Leu Asp Asp Glu Glu Gly Leu Pro Glu Lys Leu
225                 230                 235                 240

Val Ile Lys Asn Gln Gln Phe His Lys Glu Arg Glu Gln Pro Pro Arg
                245                 250                 255

Phe Ala Gln Pro Gly Ser Phe Glu Tyr Glu Tyr Ala Met Arg Trp Lys
                260                 265                 270
```

```
Ala Leu Ile Glu Met Glu Lys Gln Gln Gln Asp Gln Val Asp Arg Asn
        275                 280                 285

Ile Lys Glu Ala Arg Glu Lys Leu Glu Met Glu Met Glu Ala Ala Arg
    290                 295                 300

His Glu His Gln Val Met Leu Met Arg Gln Asp Leu Met Arg Arg Gln
305                 310                 315                 320

Glu Glu Leu Arg Arg Met Glu Glu Leu His Asn Gln Glu Val Gln Lys
                325                 330                 335

Arg Lys Gln Leu Glu Leu Arg Gln Glu Glu Arg Arg Arg Arg Arg Glu
                340                 345                 350

Glu Glu Met Arg Arg Gln Gln Glu Met Met Arg Arg Gln Gln Glu
                355                 360                 365

Gly Phe Lys Gly Thr Phe Pro Asp Ala Arg Glu Gln Glu Ile Arg Met
        370                 375                 380

Gly Gln Met Ala Met Gly Gly Ala Met Gly Ile Asn Asn Arg Gly Ala
385                 390                 395                 400

Met Pro Pro Ala Pro Val Pro Ala Gly Thr Pro Ala Pro Pro Gly Pro
                405                 410                 415

Ala Thr Met Met Pro Asp Gly Thr Leu Gly Leu Thr Pro Thr Thr
                420                 425                 430

Glu Arg Phe Gly Gln Ala Ala Thr Met Glu Gly Ile Gly Ala Ile Gly
            435                 440                 445

Gly Thr Pro Pro Ala Phe Asn Arg Ala Ala Pro Gly Ala Glu Phe Ala
        450                 455                 460

Pro Asn Lys Arg Arg Arg Tyr
465                 470

<210> SEQ ID NO 2
<211> LENGTH: 15
<212> TYPE: PRT
<213> ORGANISM: Artificial Sequence
<220> FEATURE:
<223> OTHER INFORMATION: PAT-LM1 epitope on nmt55

<400> SEQUENCE: 2

Ala Arg Glu Lys Leu Glu Met Glu Met Glu Ala Ala Arg His Glu
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: PAT-LM1 minimal epitope sequence
<220> FEATURE:
<221> NAME/KEY: misc_feature
<222> LOCATION: (5)..(5)
<223> OTHER INFORMATION: any amino acid

<400> SEQUENCE: 3

Glu Ala Ala Arg Xaa Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Additional PAT-LM1 epitope 1

<400> SEQUENCE: 4
```

Asp Pro Trp Tyr Met Phe Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Additional PAT-LM1 epitope 2

<400> SEQUENCE: 5

Asp Pro Trp Arg Glu Tyr Arg Gln Pro Tyr
1               5                   10

<210> SEQ ID NO 6
<211> LENGTH: 1791
<212> TYPE: DNA
<213> ORGANISM: Homo sapiens

<400> SEQUENCE: 6

```
agataccagt cggtagagga gaagtcgagg ttagagggaa ctggaggca ctttgctgtc      60
tgcaatcgaa gttgagggtg caaaaatgca gagtaataaa acttttaact tggagaagca    120
aaaccatact ccaagaaagc atcatcaaca tcaccaccag cagcagcacc accagcagca    180
acagcagcag ccgccaccac cgccaatacc tgcaaatggg caacaggcca gcagccaaaa    240
tgaaggcttg actattgacc tgaagaattt tagaaaacca ggagagaaga ccttcaccca    300
acgaagccgt ctttttgtgg gaaatcttcc tcccgacatc actgaggaag aaatgaggaa    360
actatttgag aaatatggaa aggcaggcga agtcttcatt cataaggata aggatttgg     420
ctttatccgc ttggaaaccc gaaccctagc ggagattgcc aaagtggagc tggacaatat    480
gccactccgt ggaaagcagc tgcgtgtgcg ctttgcctgc catagtgcat cccttacagt    540
tcgaaacctt cctcagtatg tgtccaacga actgctggaa gaagcctttt ctgtgtttgg    600
ccaggtagag agggctgtag tcattgtgga tgatcgagga aggccctcag gaaaaggcat    660
tgttgagttc tcagggaagc cagctgctcg gaaagctctg gacagatgca gtgaaggctc    720
cttcctgcta accacatttc tcgtcctgt gactgtggag cccatggacc agttagatga    780
tgaagaggga cttccagaga agctggttat aaaaaaccag caatttcaca aggaacgaga    840
gcagccaccc agatttgcac agcctggctc ctttgagtat gaatatgcca tgcgctggaa    900
ggcactcatt gagatggaga agcagcagca ggaccaagtg gaccgcaaca tcaaggaggc    960
tcgtgagaag ctggagatgg agatggaagc tgcacgccat gagcaccagg tcatgctaat   1020
gagacaggat ttgatgaggc gccaagaaga acttcggagg atggaagagc tgcacaacca   1080
agaggtgcaa aaacgaaagc aactggagct caggcaggag gaagagcgca ggcgccgtga   1140
agaagagatg cggcggcagc aagaagaaat gatgcggcga cagcaggaag gattcaaggg   1200
aaccttccct gatgcgagag agcaggagat tcggatgggt cagatggcta tgggaggtgc   1260
tatgggcata aacaacagag gtgccatgcc ccctgctcct gtgccagctg gtaccccagc   1320
tcctccagga cctgccacta tgatgccgga tggaactttg ggattgaccc caccaacaac   1380
tgaacgcttt ggtcaggctg ctacaatgga aggaattggg gcaattggtg gaactcctcc   1440
tgcattcaac cgtgcagctc ctggagctga atttgcccca acaaacgtc gccgatacta   1500
ataagttgca gtgtctagtt tctcaaaacc cttaaaagaa ggaccctttt tggactagcc   1560
agaattctac cctggaaaag tgttagggat tccttccaat agttagatct accctgcctg   1620
```

```
tactactcta gggagtatgc tggaggcaga gggcaaggga ggggtggtat taaacaagtc   1680
aattctgtgt ggtatattgt ttaatcagtt ctgtgtggtg cattcctgaa gtctctaatg   1740
tgactgttgg aaagggcctg gggaaaccat ggcaaagtgg atccagttag a            1791
```

```
<210> SEQ ID NO 7
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 7
gccaccatgc agagtaataa aacttttaac                                   30

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 8
ttacttgatg ttgcggtcca cttg                                         24

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 9
ttacatgacc tggtgctcat ggcg                                         24

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 10
ttagtgcagc tcttccatcc tccg                                         24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 11
ttagcgcctg cgctcttcct cctg                                         24

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 12
ttagaatcct tcctgctgtc gccg                                         24
```

```
<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 13
ttatcccata gccatctgac ccat                                          24

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 14
ttaggtacca gctggcacag gagc                                          24

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15
ttatggtggg gtcaatccca aagt                                          24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
ttaagttcca ccaattgccc caat                                          24

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 17
tcaagcctcc ttgatgttgc ggtc                                          24

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 18
tcactcacga gcctccttga tgtt                                          24

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer
```

```
<400> SEQUENCE: 19
tcacagcttc tcacgagcct cctt                                           24

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 20
tcacatctcc agcttctcac gagc                                           24

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 21
tcacatctcc atctccagct tctc                                           24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 22
tcaagcttcc atctccatct ccag                                           24

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 23
tcagcgtgca gcttccatct ccat                                           24

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 24
tcactcatgg cgtgcagctt ccat                                           24

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 25
tcactggtgc tcatggcgtg cagc                                           24

<210> SEQ ID NO 26
<211> LENGTH: 111
```

```
<212> TYPE: PRT
<213> ORGANISM: Artificial Sequence
<220> FEATURE:
<223> OTHER INFORMATION: Amino acid sequence of LM-1 heavy chain
      variable (VH) region sequence

<400> SEQUENCE: 26

Gln Thr Leu Ser Leu Thr Cys Ala Val Ser Gly Gly Ser Ile Ser Ser
1               5                   10                  15

Gly Gly Tyr Tyr Trp Ser Trp Ile Arg Gln His Pro Gly Lys Gly Leu
            20                  25                  30

Glu Trp Ile Gly Tyr Ile Tyr Tyr Ser Gly Ser Thr Tyr Tyr Asn Pro
        35                  40                  45

Ser Leu Lys Ser Arg Val Thr Ile Ser Val Asp Thr Ser Lys Asn Gln
50                  55                  60

Phe Ser Leu Lys Leu Ser Ser Val Thr Ala Ala Asp Thr Ala Val Tyr
65                  70                  75                  80

Tyr Cys Ala Arg Val Asp Ala Arg Tyr Asp Tyr Val Trp Gly Ser Tyr
                85                  90                  95

Arg Tyr Asp Ala Phe Asp Ile Trp Gly Gln Gly Thr Leu Val Thr
            100                 105                 110

<210> SEQ ID NO 27
<211> LENGTH: 129
<212> TYPE: PRT
<213> ORGANISM: Artificial Sequence
<220> FEATURE:
<223> OTHER INFORMATION: amino acid sequence encoding LM-1 heavy chain
      variable region

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Asp Ala Arg Tyr Asp Tyr Val Trp Gly Ser Tyr Arg
            100                 105                 110

Tyr Asp Ala Phe Asp Ile Trp Gly Gln Gly Thr Met Val Thr Val Ser
        115                 120                 125

Ser

<210> SEQ ID NO 28
<211> LENGTH: 113
<212> TYPE: PRT
<213> ORGANISM: Artificial Sequence
<220> FEATURE:
<223> OTHER INFORMATION: amino acid sequence encoding LM-1 light chain
      variable region

<400> SEQUENCE: 28

Gln Ser Val Leu Thr Gln Pro Pro Ser Val Ser Ala Ala Pro Gly Gln
1               5                   10                  15
```

```
Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Trp Val Phe Gly Gly Gly Thr Lys Leu Thr Val Leu Gly
                100                 105                 110

Gln

<210> SEQ ID NO 29
<211> LENGTH: 9
<212> TYPE: PRT
<213> ORGANISM: Homo sapiens

<400> SEQUENCE: 29

Gln Val Asp Arg Asn Ile Lys Glu Ala
1               5

<210> SEQ ID NO 30
<211> LENGTH: 11
<212> TYPE: PRT
<213> ORGANISM: Homo sapiens

<400> SEQUENCE: 30

Gln Val Asp Arg Asn Ile Lys Glu Ala Arg Glu
1               5                   10

<210> SEQ ID NO 31
<211> LENGTH: 13
<212> TYPE: PRT
<213> ORGANISM: Homo sapiens

<400> SEQUENCE: 31

Gln Val Asp Arg Asn Ile Lys Glu Ala Arg Glu Lys Leu
1               5                   10

<210> SEQ ID NO 32
<211> LENGTH: 15
<212> TYPE: PRT
<213> ORGANISM: Homo sapiens

<400> SEQUENCE: 32

Gln Val Asp Arg Asn Ile Lys Glu Ala Arg Glu Lys Leu Glu Met
1               5                   10                  15

<210> SEQ ID NO 33
<211> LENGTH: 17
<212> TYPE: PRT
<213> ORGANISM: Homo sapiens

<400> SEQUENCE: 33

Gln Val Asp Arg Asn Ile Lys Glu Ala Arg Glu Lys Leu Glu Met Glu
1               5                   10                  15

Met
```

```
<210> SEQ ID NO 34
<211> LENGTH: 19
<212> TYPE: PRT
<213> ORGANISM: Homo sapiens

<400> SEQUENCE: 34

Gln Val Asp Arg Asn Ile Lys Glu Ala Arg Glu Lys Leu Glu Met Glu
1               5                   10                  15

Met Glu Ala

<210> SEQ ID NO 35
<211> LENGTH: 21
<212> TYPE: PRT
<213> ORGANISM: Homo sapiens

<400> SEQUENCE: 35

Gln Val Asp Arg Asn Ile Lys Glu Ala Arg Glu Lys Leu Glu Met Glu
1               5                   10                  15

Met Glu Ala Ala Arg
            20

<210> SEQ ID NO 36
<211> LENGTH: 23
<212> TYPE: PRT
<213> ORGANISM: Homo sapiens

<400> SEQUENCE: 36

Gln Val Asp Arg Asn Ile Lys Glu Ala Arg Glu Lys Leu Glu Met Glu
1               5                   10                  15

Met Glu Ala Ala Arg His Glu
            20

<210> SEQ ID NO 37
<211> LENGTH: 25
<212> TYPE: PRT
<213> ORGANISM: Homo sapiens

<400> SEQUENCE: 37

Gln Val Asp Arg Asn Ile Lys Glu Ala Arg Glu Lys Leu Glu Met Glu
1               5                   10                  15

Met Glu Ala Ala Arg His Glu His Gln
            20                  25

<210> SEQ ID NO 38
<211> LENGTH: 14
<212> TYPE: PRT
<213> ORGANISM: Homo sapiens

<400> SEQUENCE: 38

Met Glu Ala Ala Arg His Glu His Gln Val Met Leu Met Lys
1               5                   10

<210> SEQ ID NO 39
<211> LENGTH: 14
<212> TYPE: PRT
<213> ORGANISM: Homo sapiens

<400> SEQUENCE: 39

Ala Glu Ala Ala Arg His Glu His Gln Val Met Leu Met Lys
1               5                   10

<210> SEQ ID NO 40
<211> LENGTH: 14
```

<212> TYPE: PRT
<213> ORGANISM: Homo sapiens

<400> SEQUENCE: 40

Met Ala Ala Ala Arg His Glu His Gln Val Met Leu Met Lys
1               5                   10

<210> SEQ ID NO 41
<211> LENGTH: 14
<212> TYPE: PRT
<213> ORGANISM: Homo sapiens

<400> SEQUENCE: 41

Met Glu Ala Ala Ala His Glu His Gln Val Met Leu Met Lys
1               5                   10

<210> SEQ ID NO 42
<211> LENGTH: 14
<212> TYPE: PRT
<213> ORGANISM: Homo sapiens

<400> SEQUENCE: 42

Met Glu Ala Ala Arg Ala Glu His Gln Val Met Leu Met Lys
1               5                   10

<210> SEQ ID NO 43
<211> LENGTH: 14
<212> TYPE: PRT
<213> ORGANISM: Homo sapiens

<400> SEQUENCE: 43

Met Glu Ala Ala Arg His Ala His Gln Val Met Leu Met Lys
1               5                   10

<210> SEQ ID NO 44
<211> LENGTH: 14
<212> TYPE: PRT
<213> ORGANISM: Homo sapiens

<400> SEQUENCE: 44

Met Glu Ala Ala Arg His Glu Ala Gln Val Met Leu Met Lys
1               5                   10

<210> SEQ ID NO 45
<211> LENGTH: 14
<212> TYPE: PRT
<213> ORGANISM: Homo sapiens

<400> SEQUENCE: 45

Met Glu Ala Ala Arg His Glu His Gln Ala Met Leu Met Lys
1               5                   10

<210> SEQ ID NO 46
<211> LENGTH: 14
<212> TYPE: PRT
<213> ORGANISM: Homo sapiens

<400> SEQUENCE: 46

Met Glu Ala Ala Arg His Glu His Gln Val Ala Leu Met Lys
1               5                   10

<210> SEQ ID NO 47
<211> LENGTH: 14
<212> TYPE: PRT
<213> ORGANISM: Homo sapiens

<400> SEQUENCE: 47

Met Glu Ala Ala Arg His Glu His Ala Val Met Leu Met Lys
1               5                   10

<210> SEQ ID NO 48
<211> LENGTH: 14
<212> TYPE: PRT
<213> ORGANISM: Homo sapiens

<400> SEQUENCE: 48

Met Glu Ala Ala Arg His Glu His Gln Val Met Ala Met Lys
1               5                   10

<210> SEQ ID NO 49
<211> LENGTH: 14
<212> TYPE: PRT
<213> ORGANISM: Homo sapiens

<400> SEQUENCE: 49

Met Glu Ala Ala Arg His Glu His Gln Val Met Leu Ala Lys
1               5                   10

<210> SEQ ID NO 50
<211> LENGTH: 13
<212> TYPE: PRT
<213> ORGANISM: Homo sapiens

<400> SEQUENCE: 50

Met Glu Ser Ala His Glu His Gln Val Met Leu Met Lys
1               5                   10

<210> SEQ ID NO 51
<211> LENGTH: 14
<212> TYPE: PRT
<213> ORGANISM: Homo sapiens

<400> SEQUENCE: 51

Met Glu Ala Ser Arg His Ala His Gln Val Met Leu Met Lys
1               5                   10

<210> SEQ ID NO 52
<211> LENGTH: 14
<212> TYPE: PRT
<213> ORGANISM: Homo sapiens

<400> SEQUENCE: 52

Met Glu Ala Ala Ala His Glu His Gln Ala Met Leu Met Lys
1               5                   10

<210> SEQ ID NO 53
<211> LENGTH: 14
<212> TYPE: PRT
<213> ORGANISM: Homo sapiens

<400> SEQUENCE: 53

Met Glu Ala Ala Arg His Ala His Gln Val Ala Leu Met Lys
1               5                   10

<210> SEQ ID NO 54
<211> LENGTH: 60
<212> TYPE: DNA
<213> ORGANISM: Homo sapiens

<400> SEQUENCE: 54
atggctctgg atccttggta tatgtttcgt aatagtggtc ataatcataa tcataatcat    60

<210> SEQ ID NO 55
<211> LENGTH: 57
<212> TYPE: DNA
<213> ORGANISM: Homo sapiens

<400> SEQUENCE: 55
atgctggatc cttggtatat gtttcgtaat agtggtcata atcataatca taatcat    57

<210> SEQ ID NO 56
<211> LENGTH: 54
<212> TYPE: DNA
<213> ORGANISM: Homo sapiens

<400> SEQUENCE: 56
atggatcctt ggtatatgtt tcgtaatagt ggtcataatc ataatcataa tcat    54

<210> SEQ ID NO 57
<211> LENGTH: 51
<212> TYPE: DNA
<213> ORGANISM: Homo sapiens

<400> SEQUENCE: 57
atgccttggt atatgtttcg taatagtggt cataatcata atcataatca t    51

<210> SEQ ID NO 58
<211> LENGTH: 48
<212> TYPE: DNA
<213> ORGANISM: Homo sapiens

<400> SEQUENCE: 58
atgtggtata tgtttcgtaa tagtggtcat aatcataatc ataatcat    48

<210> SEQ ID NO 59
<211> LENGTH: 60
<212> TYPE: DNA
<213> ORGANISM: Homo sapiens

<400> SEQUENCE: 59
atggatgctc tggatccttg gtatatgttt cgtaatggtc ataatcataa tcataatcat    60

<210> SEQ ID NO 60
<211> LENGTH: 57
<212> TYPE: DNA
<213> ORGANISM: Homo sapiens

<400> SEQUENCE: 60
atggatgctc tggatccttg gtatatgttt cgtggtcata atcataatca taatcat    57

<210> SEQ ID NO 61
<211> LENGTH: 54
<212> TYPE: DNA
<213> ORGANISM: Homo sapiens

<400> SEQUENCE: 61
atggatgctc tggatccttg gtatatgttt ggtcataatc ataatcataa tcat    54

<210> SEQ ID NO 62
<211> LENGTH: 60
<212> TYPE: DNA
<213> ORGANISM: Homo sapiens

```
<400> SEQUENCE: 62
atgtatgatc cgtggcgtga gtatcggcag ccgtatggtc ataatcataa tcataatcat      60

<210> SEQ ID NO 63
<211> LENGTH: 57
<212> TYPE: DNA
<213> ORGANISM: Homo sapiens

<400> SEQUENCE: 63
atggatccgt ggcgtgagta tcggcagccg tatggtcata atcataatca taatcat          57

<210> SEQ ID NO 64
<211> LENGTH: 54
<212> TYPE: DNA
<213> ORGANISM: Homo sapiens

<400> SEQUENCE: 64
atgccgtggc gtgagtatcg gcagccgtat ggtcataatc ataatcataa tcat             54

<210> SEQ ID NO 65
<211> LENGTH: 60
<212> TYPE: DNA
<213> ORGANISM: Homo sapiens

<400> SEQUENCE: 65
atgttttatg atccgtggcg tgagtatcgg cagccgggtc ataatcataa tcataatcat      60

<210> SEQ ID NO 66
<211> LENGTH: 57
<212> TYPE: DNA
<213> ORGANISM: Homo sapiens

<400> SEQUENCE: 66
atgttttatg atccgtggcg tgagtatcgg cagggtcata atcataatca taatcat          57

<210> SEQ ID NO 67
<211> LENGTH: 54
<212> TYPE: DNA
<213> ORGANISM: Homo sapiens

<400> SEQUENCE: 67
atgttttatg atccgtggcg tgagtatcgg ggtcataatc ataatcataa tcat             54
```

PAT-LM1 EPITOPES AND METHODS FOR USING SAME

FIELD OF THE DISCLOSURE

The disclosure relates to epitopes and mimotopes of an antibody known as PAT-LM1, and methods for using said epitopes and mimotopes.

BACKGROUND OF THE DISCLOSURE

The antibody denoted PAT-LM1 (as deposited with DSMZ under accession number DSM ACC 2623; also referred to herein as "LM1") is an IgM and binds to different types of neoplasias, cancers, tumors, or metastases thereof. PAT-LM1 inhibits growth of various types of cancer cells and stimulates or induces apoptosis of various types of cancer cells. PAT-LM1 also reduces formation or establishment of metastases at one or more sites arising from a primary neoplasm, tumor or cancer, or growth or proliferation of a metastasis that has formed or been established at one or more other sites.

PAT-LM1 antibody, variants, functional fragments and target antigen (NMT55, also known as nuclear matrix protein 55; NONO (non-pou domain-containing octamer-binding protein); p54nrb (54 kDa nuclear RNA- and DNA-binding protein); or 55 kDa nuclear protein) have been identified previously (see. WO 2004/081027 and WO 2010/004438). However, there remains a need to identify specific PAT-LM1 epitopes. An understanding of PAT-LM1 epitopes will aid in the development of anti-cancer therapies. The present disclosure addresses these needs.

SUMMARY OF DISCLOSURE

The present inventors have used the PAT-LM1 antibody to identify epitopes on NMT55 and mimotopes thereof, which are useful agents for treating or preventing proliferative disorders.

Accordingly, the present disclosure provides an isolated peptide of about 6 to 50 amino acids comprising an amino acid sequence shown in any one of SEQ ID NOs: 3, 4 or 5. The present disclosure further provides an isolated peptide comprising an amino acid sequence having at least 90%, more preferably, at least 95%, 96%, 97%, 98%, or 99% identity to an amino acid sequence shown in any one of SEQ ID NOs: 3, 4 or 5. The present disclosure further provides an isolated peptide comprising an amino acid sequence shown in any one of SEQ ID NOs: 3, 4 or 5 having one or more conservative amino acid substitutions, for example, 1 or 2 or 3 or 4 conservative amino acid substitutions. The present disclosure further provides an isolated peptide consisting of an amino sequence shown in any one of SEQ ID NOs: 3, 4 or 5.

The present disclosure also provides an isolated and/or exogenous nucleic acid encoding at least one peptide of the disclosure.

The present disclosure also provides a composition comprising a peptide of the present disclosure. In an embodiment, the composition further comprises a pharmaceutically acceptable carrier such as an adjuvant. In a further embodiment, the composition induces or enhances an immune response.

The present disclosure also provides a vaccine comprising a peptide of the present disclosure or a nucleic acid encoding therefor. In an embodiment, the vaccine further comprises a pharmaceutically acceptable carrier such as an adjuvant.

The present disclosure also provides a method of inducing an immune response in a subject comprising administering a peptide or nucleic acid encoding therefor, composition, or vaccine of the present disclosure to said subject.

In an embodiment of the present disclosure, the subject has or is at risk of having a proliferative disorder, for example, a neoplasia, cancer, tumor, or metastasis thereof. The cancer may be, for example, colorectal cancer, ovarian carcinoma, squamous cell lung carcinoma, small cell lung carcinoma, lobular and ductal mammary carcinomas, melanoma, breast cancer, lung cancer, such as lung adenocarcinomas, gastric cancer, pancreatic cancer, such as pancreatic adenocarcinomas, glioma, sarcomas, gastrointestinal cancer, brain tumor, esophageal cancer, such as esophagial squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias.

In an embodiment, the peptide or nucleic acid encoding therefor, composition, or vaccine of the disclosure reduces the size and/or growth of a neoplasia, cancer, tumor, or metastasis thereof in the subject. In an embodiment, the peptide or nucleic acid encoding therefor, composition, or vaccine of the disclosure prevents the initiation of a neoplasia or tumor growth or cancer. In an embodiment, the peptide or composition of the disclosure prevents the metastasis of, or delays onset of the metastasis of the neoplasia, tumor, or cancer in the subject.

The present disclosure also provides a method for treating a proliferative disorder in a subject, the method comprising administering to a subject the peptide of the disclosure, the nucleic acid of the disclosure, the composition of the disclosure, or the vaccine of the disclosure.

In a further embodiment, the method for treating a proliferative disorder in a subject further comprises administering to the subject an anti-neoplastic agent. The anti-neoplastic agent may be for example, radiation or chemotherapy.

Also provided is the use of the peptide of the disclosure, the nucleic acid of the disclosure, the composition of the disclosure, or the vaccine of the disclosure for the manufacture of a medicament for inducing an immune response in a subject.

Also provided is the use of the peptide of the disclosure, the nucleic acid of the disclosure, the composition of the disclosure, or the vaccine of the disclosure for inducing an immune response in a subject.

Also provided is the use of the peptide of the disclosure, the nucleic acid of the disclosure, the composition of the disclosure, or the vaccine of the disclosure for the manufacture of a medicament for the treatment of a proliferative disorder in a subject.

Also provided is the use of the peptide of the disclosure, the nucleic acid of the disclosure, the composition of the disclosure, or the vaccine of the disclosure for the treatment of a proliferative disorder in a subject.

The present disclosure also provides a method for assaying, enriching, isolating or purifying a compound (e.g., an antibody or antigen binding fragment thereof) which comprises contacting the compound with a peptide of the present disclosure.

In an embodiment, the method is for assaying the level of a compound in a sample and comprises detecting the level of the compound in the sample.

In one example, the compound is an antibody or antigen binding fragment.

In one example, detection of the antibody or antigen binding fragment may be determined by contacting the antibody or antigen binding fragment thereof, under conditions to effect specific binding of the antibody or antigen binding fragment thereof to form a complex and detecting the amount of the complex, for example, by Western blot or ELIZA.

In an embodiment, the method additionally comprises isolating or obtaining a biological sample from the subject and detecting the level of the compound in the sample. The sample may be, for example, a biological fluid such as urine, blood, plasma, serum, saliva, ascites and the like. The method may be performed, for example, in vitro or ex vivo.

In another embodiment, the method is for enriching, isolating or purifying a compound and comprises selecting a compound or a cell expressing same or particle displaying same that binds to the peptide of the disclosure.

In one example, the compound is an antibody or antigen binding fragment thereof.

In one example, the antibody or antigen binding fragment is chimeric, humanized or human.

In one example, the method additionally comprises reformatting the antigen binding fragment to thereby produce an antibody.

In one example, the method additionally comprises manufacturing the compound and, optionally, preparing a composition comprising the compound (e.g., an antibody or antigen binding fragment thereof) and a pharmaceutically acceptable carrier.

In an embodiment, the present disclosure provides an assay which comprises contacting (e.g., an antibody or antigen binding fragment thereof) at least one peptide of the present invention with a sample and detecting whether a compound in the sample specifically binds the peptide.

In an embodiment, the present disclosure provides a substrate which comprises the peptide of the present disclosure immobilized thereon.

The substrate may be made from a variety of materials including silicon, silica, quartz, glass, controlled pore glass, carbon, alumina, titania, tantalum oxide, germanium, silicon nitride, zeolites, gallium arsenide, gold, platinum, aluminum, copper and titanium, polymers, combinations thereof, and the like. The substrates are preferably made of materials that do not substantially affect any assay and reagents in which the substrates of the present invention are employed. In preferred embodiments, the substrates comprise polymers such as polystyrene; poly(tetra)fluoroethylene (PTFE); polyvinylidenedifluoride; polycarbonate (PC); polymethylmethacrylate (PMMA); polyvinylethylene; polyethyleneimine; poly(etherether)ketone; polyoxymethylene (POM); polyvinylphenol; polylactides; polymethacrylimide (PMI); polyetherimide (PEI), cyclo-olefin, polyalkenesulfone (PAS); polypropylene; polyethylene; polyhydroxyethylmethacrylate (HEMA); polydimethylsiloxane (PDMS); polyacrylamide; polyimide; and block-copolymers, and the like, and combinations thereof.

The present invention provides a kit comprising at least one peptide of the present disclosure packaged together with at least one reagent, such those used in immunoassays to detect binding of the peptides to a compound (e.g., an antibody). The kit may also include instructions for use.

The present disclosure further provides a method of screening for a compound (e.g., an antibody or antigen binding fragment thereof) that binds a peptide of the disclosure.

For example, the method comprises screening a library, for example, a phage display library.

The present disclosure further provides a method for detecting, diagnosing, or monitoring a cancer in a subject which comprises contacting a peptide of the present disclosure with a sample obtained from the subject and determining whether an antibody in the sample specifically binds the peptide.

The sample may be, for example, a biological fluid such as urine, blood, plasma, serum, saliva, ascites and the like.

In one example, the cancer expresses NMT55. The cancer may be, for example, colorectal cancer, ovarian carcinoma, squamous cell lung carcinoma, small cell lung carcinoma, lobular and ductal mammary carcinomas, melanoma, breast cancer, lung cancer, such as lung adenocarcinomas, gastric cancer, pancreatic cancer, such as pancreatic adenocarcinomas, glioma, sarcomas, gastrointestinal cancer, brain tumor, esophageal cancer, such as esophagial squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias.

In one embodiment, the method additionally comprises isolating or obtaining a biological sample from the subject.

In one example, detection of the antibody in the sample may be determined by contacting the antibody, under conditions to effect specific binding of the antibody to form a complex and detecting the amount of the complex, for example, by Western blot or ELIZA.

The present disclosure further provides a compound such as an antibody or antigen binding fragment thereof that binds to a peptide of the disclosure. The present disclosure further provides for use of this compound in the methods of the disclosure, for example, diagnosing and treating a neoplasia, cancer, or tumor, or metastasis thereof in a subject.

BRIEF DESCRIPTION OF THE DRAWINGS

FIG. 1 shows the strategy used to clone fragments of NMT55 for mapping the PAT-LM1 epitope, as described in Example 1 and as outlined in FIG. 2. Highlighted in bold is the sequence comprising the PAT-LM1 epitope sequence on NMT55 (SEQ ID NO: 3).

FIG. 5 shows the strategy used to fine map the PAT-LM1 epitope sequence of "Epitope 1" identified through phage display experiments (A). (LM1-epi-1.1 (SEQ ID NO:54); LM1-epi-1.2 (SEQ ID NO:55); LM1-epi-1.3 (SEQ ID NO:56); LM1-epi-1.3.1 (SEQ ID NO:57); LM1-epi-1.3.2 (SEQ ID NO:58); LM1-epi-1.4 (SEQ ID NO:59); LM1-epi-1.5 (SEQ ID NO:60); LM1-epi-1.6 (SEQ ID NO:61). B, C and D) are Western blots showing that PAT-LM1-Epi-1.1, PAT-LM1-Epi-1.2, PAT-LM1-Epi-1.3, PAT-LM1-Epi-1.4 and PAT-LM1-Epi-1.5 were the only polypeptides to show binding to PAT-LM1 antibody. PAT-LM1-Epi-1.3.1, PAT-LM1-Epi-1.3.2 and PAT-LM1-Epi-1.6 failed to show binding to PAT-LM1 antibody.

FIG. 6 shows the strategy used to fine map the PAT-LM1 epitope sequence of "Epitope 2" identified through phage display experiments (A) (LM1-epi-2.1 (SEQ ID NO:62); LM1-epi-2.2 (SEQ ID NO:63); LM1-epi-2.3 (SEQ ID NO:64); LM1-epi-2.4 (SEQ ID NO:65); LM1-epi-2.5 (SEQ ID NO:66); LM1-epi-2.6 (SEQ ID NO:67)). B and C) are Western blots showing that PAT-LM1-Epi-2.1 and LM-Epi-2.2 were the only polypeptides to show binding to PAT-LM1 antibody. PAT-LM1-Epi-2.3, PAT-LM1-Epi-2.4, PAT-LM1-Epi-2.5 and PAT-LM1-Epi-2.6 failed to show binding to PAT-LM1 antibody.

KEY TO THE SEQUENCE LISTING

Figure 2:
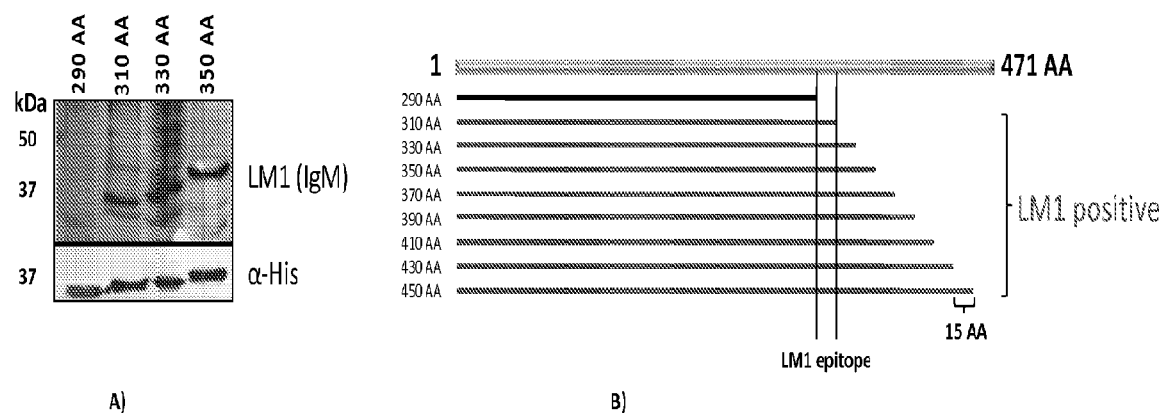
FIG. 2 shows the strategy used for scanning overlapping fragments derived from the amino acid sequence of the PAT-LM1 antigen (NMT55) for epitope mapping. A) Western blot showing that fragment 3 comprising amino acids 290-471 of NMT55 was identified as being bound by PAT-LM1. B) The NMT55 subcloning strategy. NMT55 was subcloned into ten 15 amino acid reduced fragments. The subfragment comprising amino acids 1-310 of NMT55 was identified as the last positive PAT-LM1 construct. Thus, the PAT-LM1 epitope mapped between amino acids 290-310 of NMT55.

SEQ ID NO: 1—amino acid sequence of human NMT55 (GenBank Accession No: U89867.1; UniProt Accession No: Q15233).
SEQ ID NO: 2—amino acid sequence comprising the PAT-LM1 epitope (amino acids 292-306 of NMT55).
SEQ ID NO: 3—amino acid sequence of the minimal PAT-LM1 epitope.
SEQ ID NO: 4—amino acid sequence of additional PAT-LM1 epitope 1 (mimotope 1).
SEQ ID NO: 5—amino acid sequence of additional PAT-LM1 epitope 2 (mimotope 2).
SEQ ID NO: 6—DNA encoding human NMT55 (GenBank Accession No: U89867.1; UniProt Accession No: Q15233).
SEQ ID NOs: 7-25—Oligonucleotide primers.
SEQ ID NO:26:—amino acid sequence of the heavy chain variable region of PAT-LM1.
SEQ ID NO:27:—amino acid sequence of the heavy chain variable region of PAT-LM 1.
SEQ ID NO:28:—amino acid sequence of the light chain variable region of PAT-LM1.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Any example of the present disclosure disclosing a specific feature or group of features or method or method steps will be taken to provide explicit support for disclaiming the specific feature or group of features or method or method steps.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

The description and definitions of variable regions and parts thereof, antibodies and fragments thereof herein may be further clarified by the discussion in Kabat Sequences of Proteins of Immunological Interest, National Institutes of Health, Bethesda, Md., 1987 and 1991.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SELECTED DEFINITIONS

The term "immunoglobulin" will be understood to include any antigen binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors.

The skilled artisan will be aware that an "antibody" is generally considered to be a protein that comprises a variable region made up of a plurality of polypeptide chains, for example, a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that specifically binds to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one embodiment, the antibody is an IgM. The term "antibody" also encompasses humanized antibodies, primatized antibodies, human antibodies and chimeric antibodies.

The term "full-length antibody" refers to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof. In some cases, the intact antibody may be capable of inducing one or more effector functions.

An "antigen binding fragment" of an antibody comprises one or more variable regions of a full-length antibody. Examples of antibody fragments include Fab, Fab', F(ab')$_2$ and Fv fragments; diabodies; linear antibodies; single-chain antibody molecules and multispecific antibodies formed from antibody fragments.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies or antigen binding fragments thereof include: complement dependent cytotoxicity; antibody-dependent-cell-mediated cytotoxicity (ADCC); antibody-dependent-cell-phagocytosis (ADCP); and B-cell activation.

"Antibody-dependent-cell-mediated cytotoxicity" or "ADCC" refers to a form of cytotoxicity in which secreted Ig bound onto Fc receptors ("FcRs") present on certain cytotoxic cells (e.g., natural killer ("NK") cells, neutrophils and macrophages) enable these cytotoxic effector cells to bind specifically to an antigen-bearing target-cell and subsequently kill the target-cell with cytotoxins. To assess ADCC activity of a molecule of interest, an in vitro ADCC assay may be performed. Useful effector cells for such assays include peripheral blood mononuclear cells ("PBMC").

As used herein, "variable region" refers to the portions of the light and/or heavy chains of an antibody as defined herein that specifically binds to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system". According to the numbering system of Kabat, $V_H$ FRs and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4).

"Framework regions" (hereinafter FR) are those variable domain residues other than the CDR residues.

The term "constant region" as used herein, refers to a portion of heavy chain or light chain of an antibody other than the variable region. In a heavy chain, the constant region generally comprises a plurality of constant domains and a hinge region, e.g., a IgG constant region comprises the following linked components, a constant heavy ($C_H$)1, a linker, a $C_H$2 and a $C_H$3. In a heavy chain, a constant region comprises a Fc. In a light chain, a constant region generally comprise one constant domain (a $C_L$1).

The term "fragment crystalizable" or "Fc" or "Fc region" or "Fc portion" (which can be used interchangeably herein) refers to a region of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, for example, the constant region of γ, α or δ heavy chain comprises two constant domains.

The term "EU numbering system of Kabat" will be understood to mean the numbering of an antibody heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

Reference herein to "PAT-LM1 antibody" or to "LM1" is a reference to the antibody deposited with DSMZ under accession number DSM ACC 2623 and described in WO 2004/081027 and/or WO 2010/004438. The LM1 antibody comprises the heavy and light chain variable region sequences shown in SEQ ID NO: 26 and 28, or SEQ ID NO: 27 and 28, respectively.

As used herein, the term "specific binding" shall be taken to mean an antibody or antigen binding fragment thereof that reacts or associates more frequently, more rapidly, with greater duration and/or with greater affinity with a peptide of the disclosure, antigen comprising said peptide (e.g., NMT55), or cell expressing said peptide or antigen, than it does with alternative peptides, antigens, or cells. For example, an antibody that specifically binds to a peptide of the disclosure, antigen comprising said peptide, or cell expressing said peptide or antigen, binds that peptide, antigen, or cell with greater affinity, avidity, more readily, and/or with greater duration than it binds to other peptides, antigens or cells. It is also understood that, for example, an antibody that specifically binds to said peptide, antigen, or cell may or may not specifically bind to a second peptide, antigen, or cell. As such, "specific binding" does not necessarily require exclusive binding or non-detectable binding of another molecule, this is meant by the term "selective binding". Generally, but not necessarily, reference to binding means specific binding, and each term shall be understood to provide explicit support for the other term.

As used herein, the term "does not detectably bind" shall be understood to mean that an antibody or antigen binding fragment thereof of the disclosure binds to a candidate peptide or antigen (e.g., NMT55) at a level less than 10%, or 8% or 6% or 5% above background. The background can be the level of binding signal detected in the absence of the antibody or antigen binding fragment and/or in the presence of a negative control peptide or protein and/or the level of binding detected in the presence of a negative control peptide or antigen. The level of binding is detected using Western Blotting and/or FACS analysis of cells expressing the peptide or antigen or lacking expression of the peptide or antigen.

The term "competitively inhibits" shall be understood to mean that an antibody or antigen binding fragment thereof of the disclosure reduces or prevents binding of a recited antibody to NMT55 or a peptide of the disclosure. It will be apparent from the foregoing that the antibody or antigen binding fragment thereof need not completely inhibit binding of the recited antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art. For example, the antibody is exposed to NMT55 or a peptide of the disclosure either in the presence or absence of a test antibody or antigen binding fragment thereof. If less of the antibody binds in the presence of the test antibody or antigen binding fragment than in the absence of the test antibody or antigen binding fragment, the antibody or antigen binding fragment is considered to competitively inhibit binding of the antibody.

As used herein, the term "NMT55-mediated condition" will be understood to mean a condition associated with or caused by excessive NMT55 expression and/or an excessive number of NMT55 expressing cells in a mammal, such as neoplastic or cancer cells.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

As used herein, a subject "at risk" of developing a disease or condition or relapse thereof or relapsing may or may not have detectable disease or symptoms of disease, and may or may not have displayed detectable disease or symptoms of disease prior to the treatment according to the present disclosure. "At risk" denotes that a subject has one or more risk factors, which are measurable parameters that correlate with development of the disease or condition, as known in the art.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition such as a proliferative disorder, for example, cancer. The effective amount may vary according to the disease or condition to be treated and also according to the weight, age, racial background, sex, health and/or physical condition and other factors relevant to the mammal being treated. Typically, the effective amount will fall within a relatively broad range (e.g., a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g., cancer). A therapeutically effective amount herein may vary according to factors such as the disease state, age, sex, and weight of the patient, and the ability of the vaccine or antibody or antigen binding fragment thereof to elicit a desired response in the individual. A therapeutically effective amount is also one in which any toxic or detrimental effects of the vaccine or antibody or antigen binding fragment thereof are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in subjects prior to or at an earlier stage of disease, a prophylactically effective amount may be less than a therapeutically effective amount.

The term "immune response" has its ordinary meaning in the art, and includes both humoral and cellular immunity. An immune response can manifest as one or more of, the development of anti-antigen antibodies, expansion of antigen-specific T cells, increase in tumor infiltrating-lymphocytes (TILs); development of an anti-tumor or anti-tumor antigen delayed-type hypersensitivity (DTH) response, clearance of the pathogen, suppression of pathogen and/or tumor growth and/or spread, tumor reduction, reduction or elimination of metastasis, increased time to relapse, increased time of pathogen or tumor free survival, and increased time of survival. An immune response may be mediated by one or more of, B-cell activation. T-cell activation, natural killer cell activation, activation of antigen presenting cells (e.g., B cells, DCs, monocytes and/or macrophages), cytokine production, chemokine production, specific cell surface marker expression, in particular, expression of co-stimulatory molecules. The immune response may be characterized by a humoral, cellular, Th1 or Th2 response, or combinations thereof.

The "subject" treated according to the present disclosure may be a mammal, such as a non-human primate or a human. In one example, the mammal is a human.

The terms "tumor," "cancer" and "neoplasia" are used interchangeably and refer to a cell or population of cells whose growth, proliferation or survival is greater than growth, proliferation or survival of a normal counterpart cell, for example, a cell proliferative or differentiative disorder. Typically, the growth is uncontrolled. The term "malignancy" refers to invasion of nearby tissue. The term "metastasis" refers to spread or dissemination of a tumor, cancer, or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

The term "identity" and grammatical variations thereof, mean that two or more referenced entities are the same. Thus, where two protein or polypeptide sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. An "area of identity" refers to a portion of two or more referenced entities that are the same. Thus, where two protein, polypeptide or nucleic acid sequences are identical over one or more sequence regions they share identity within that region. Exemplary identity are proteins or polypeptides or functional fragments thereof with an amino acid sequence with 50%, 60%, 70%, 75%, 80%, 85%, 90%, 95%, 96%, 97%, 98%, 99% or more sequence identity to a reference protein or polypeptide or functional fragments thereof.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

The terms "homologous" or "homology" mean that two or more referenced entities share at least partial identity over a given region or portion.

"Areas, regions or domains" of homology or identity mean that a portion of two or more referenced entities share homology or are the same. Thus, where two antibody sequences are identical over one or more sequence regions they share identity in these regions.

"Substantial homology" means that a molecule is structurally or functionally conserved such that it has or is predicted to have at least partial structure or function of one or more of the structures or functions (e g, a biological function) of the reference molecule, or relevant/corresponding region or portion of the reference molecule to which it shares homology. A protein, polypeptide or functional fragment with substantial homology has or is predicted to have at least partial activity or function as the reference protein or polypeptide.

The extent of identity or homology between two sequences can be ascertained using a computer program and mathematical algorithm known in the art. Such algorithms that calculate percent sequence identity or homology generally account for sequence gaps and mismatches over the comparison region or area. For example, a BLAST (e.g., BLAST 2.0) search algorithm (see, e.g., Altschul et al., 1990, publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., 1988; Pearson 2000; and Smith et al., 1981). Programs for quantitating protein structural similarity using Delaunay-based topological mapping have also been developed (Bostick et al., 2003).

NMT55

The PAT-LM1 antibody was found previously to recognise NMT55 as its target (see WO 2010/004438). NMT55 is also known in the art as nuclear matrix protein 55, NONO (non-pou domain-containing octamer-binding protein), p54nrb (54 kDa nuclear RNA- and DNA-binding protein) or 55 kDa nuclear protein.

NMT55 is a nuclear protein, expressed on cancer, tumor and malignant cells. PAT-LM1 binds to the N-terminal region of NMT55. PAT-LM1 binding to NMT55 induces apoptosis of the cells to which it binds.

NMT55 is a DNA- and RNA-binding protein, involved in several nuclear processes. It binds the conventional octamer sequence in double stranded DNA. It also binds single-stranded DNA and RNA at a site independent of the duplex site. NMT55 is involved in pre-mRNA splicing, probably as an heterodimer with SFPQ (splicing factor, proline and glutamine-rich protein). NMT55 interacts with U5 snRNA, likely by binding to a purine-rich sequence located on the 3' side of U5 snRNA stem 1b. The SFPQ-NMT55 heteromer associated with MATR3 may play a role in nuclear retention of defective RNAs. The SFPQ-NMT55 heteromer may be involved in DNA unwinding by modulating the function of topoisomerase I/TOP1. The SFPQ-NMT55 heteromer may be involved in DNA non-homologous end joining (NHEJ) required for double-strand break repair and V(D)J recombination and may stabilize paired DNA ends. In vitro, the complex strongly stimulates DNA end joining, binds directly to the DNA substrates and cooperates with the Ku70/G22P1-Ku80/XRCC5 (Ku) dimer to establish a functional pre-ligation complex. NMT55 is also involved in transcriptional regulation. The SFPQ-NMT55-NR5A1 complex binds to the CYP17 promoter and regulates basal and cAMP-dependent transcriptional activity. NMT55 binds to an enhancer element in long terminal repeats of endogenous intracisternal A particles (IAPs) and activates transcription.

The canonical NMT55 sequence, containing 471 amino acids (54.2 kDa), is provided in SEQ ID NO: 1 (GenBank Accession No: U89867.1 or UniProt Accession No: Q15233). NMT55 is predicted to have different isoforms (for example, UniProt Accession Nos: C9JYS8, C9JRA5, B7Z4C2 and B4DWI8). However, since these isoforms have been predicted from automatic sequence prediction programs and there is a lack of functional data to support the predictions, sequences of these isoforms are continually being revised and updated. As used herein, the term NMT55 is used to refer to the canonical NMT55 sequence.

Compounds
Antibodies
Immunization-Based Methods

Methods for generating antibodies are known in the art and/or described in Harlow and Lane (editors) Antibodies: A Laboratory Manual, Cold Spring Harbor Laboratory, (1988). Generally, in such methods a peptide of the disclosure (which comprises an epitope or mimotope of NMT55), antigen comprising said peptide (e.g., NMT55), or cell expressing said peptide or antigen and displaying same (i.e., an immunogen), optionally formulated with any suitable or desired carrier, adjuvant, or excipient, is administered to a non-human animal, for example, a mouse, chicken, rat, rabbit, guinea pig, dog, horse, cow, goat or pig. The immunogen may be administered intranasally, intramuscularly, subcutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

Monoclonal antibodies are one exemplary form of antibody contemplated by the present disclosure. The term "monoclonal" when used in reference to an antibody refers to a homogeneous antibody population capable of binding to the same antigen(s), for example, to the same epitope within the antigen. Such antibodies may be based upon, obtained from or derived from a single clone, including any eukaryotic, prokaryotic, or phage clone. The term "monoclonal" is not intended to be limited as to the source of the antibody or the manner in which it is made. For the production of Mabs any one of a number of known techniques may be used, such as, for example, the procedure exemplified in U.S. Pat. No. 4,196,265 or Harlow and Lane (1988), supra.

For example, a suitable animal is immunized with an immunogen (e.g., a peptide of the disclosure) under conditions sufficient to stimulate antibody producing cells. Rodents such as rabbits, mice and rats are exemplary animals. Mice genetically-engineered to express human immunoglobulin proteins and, for example, do not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal neoplastic cell such as a myeloma, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemistry and/or immunoassay (e.g., radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al., 1996).

Hybridoma Cell Lines

Monoclonal antibodies, such as monoclonal antibodies that specifically bind peptides of the disclosure, may be produced by hybridoma cell lines. A "hybridoma," as used herein, is any cell that is artificially created by the fusion of a normal cell such as an activated lymphocyte with a neoplastic cell, for example, a myeloma. The hybrid cell, which results from the fusion of at least two cells, may produce a monoclonal antibody or T cell product identical to those produced by the immunologically-competent parent. In addition, these cells, like the neoplastic parent, are immortal.

Such cell lines are typically generated by the fusion of spleen and lymph node lymphocytes derived from patients having a neoplasm, such as colon carcinoma or a pancreatic carcinoma, with a heteromyeloma cell line. Exemplary heteromyeloma cell lines include, for example, HAB-1 (Vollmers et al., 1994), CB-F7 (Delvig et al., 1995), K6H6B5 (Delvig et al., 1995), H7NS.934 (Delvig et al., 1995), SHM-D33 (Bron et al., 1984), and B6B11 (Borisova et al., 1999). The ability to generate human monoclonal antibodies from lymphocytes of cancer patients allows the isolation of antibodies that are generated by an immune response in the cancer patient to the tumor.

Typically, portions of the lymph nodes or spleen are surgically removed from a patient having cancer, such as colon carcinoma or a pancreatic carcinoma. Lymphocytes may be prepared as cell suspensions by mechanical means and subsequently fused at, for example, a 1:2 or 1:3 ratio with a heteromyeloma cell line under conditions that result in cell fusion. For instance, the heteromyeloma cell line HAB-1, which is generated by the fusion of a human lymphocyte with the mouse myeloma NS-0, may be used for this purpose. A proportion of lymphocytes isolated from the cancer patient may also be maintained in culture. These cells serve as a source of human autologous cells useful for the initial antibody screening described below.

Following the fusion of the lymphocytes derived from the cancer patient with the heteromyeloma cell line, an antibody producing hybridoma or trioma is generated. Once constructed, hybridomas are generally stable in growth and antibody production in standard and mass cultures (flasks, miniPerm, fermenters, etc.) for several months. Levels of antibody production typically range between 0.01-0.1 mg/mL in flasks and between 0.1-0.5 mg/mL in miniPerm. Cell fusion may be achieved by any method known in the art, and includes, for example, the use of 40% polyethylene glycol. Hybridomas may be cultured in media containing HAT (Hypovanthin-aminopterin-thymidine) and after four weeks, supernatants may be screened for antibody production using an ELISA assay. Positive clones may then be tested in attachment inhibition and binding assays using autologous cell lines as prepared above. Positive clones further may be tested using immunoperoxidase staining of tumor and normal tissues. Thus, clones may be selected on the basis of their reactivity with autologous and allogeneic neoplastic cells. The antibody may be purified from mass cultures with use of cation-exchange chromatography followed by gel filtration as described, for example, by Vollmers et al., 1998. Following the production of antibodies, additional functional and immunohistochemical tests of the antibodies produced by the trioma may be performed. For example, the antibodies produced by the hybridoma can be tested for their ability to induce apoptosis, inhibit cellular proliferation, or both, relative to untreated control cells.

Library-Based Methods

The present disclosure also encompasses screening of libraries of antibodies or antigen binding fragments thereof (e.g., comprising variable regions thereof).

Examples of libraries contemplated by this disclosure include naïve libraries (from unchallenged subjects), immunized libraries (from subjects immunized with a peptide or antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. No. 5,885,793, U.S. Pat. No. 6,204,023, U.S. Pat. No. 6,291,158, or U.S. Pat. No. 6,248,516.

The antigen binding fragments according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding fragments of antibodies are expressed on phage, for example, as described in U.S. Pat. No. 6,300,064, U.S. Pat. No. 5,885,793, U.S. Pat. No. 6,204,023, U.S. Pat. No. 6,291,158, or U.S. Pat. No. 6,248,516. Other phage display methods are known in the art and are contemplated by the present disclosure. Similarly, methods of cell display are contemplated by the disclosure, for example, bacterial display libraries, for example, as described in U.S. Pat. No. 5,516,637; yeast display libraries, for example, as described in U.S. Pat. No. 6,423,538; or a mammalian display library.

Methods for screening display libraries are known in the art. In one example, a display library of the present disclosure is screened using affinity purification, for example, as described in Scopes (In: Protein purification: principles and practice, Third Edition, Springer Verlag, 1994). Methods of affinity purification typically involve contacting proteins comprising antigen binding fragments displayed by the library with a target peptide or antigen (e.g., NMT55) and, following washing, eluting those domains that remain bound to the peptide or antigen.

Any variable regions or scFvs identified by screening are readily modified into a complete antibody, if desired. Exemplary methods for modifying or reformatting variable regions or scFvs into a complete antibody are described, for example, in Jones et al., 2010; or Jostock et al., 2004; or WO 2012/040793. Alternatively, or additionally, standard cloning methods are used, for example, as described in Ausubel et al., (In: Current Protocols in Molecular Biology. Wiley Interscience, ISBN 047 150338, 1987), and/or (Sambrook et al., (In: Molecular Cloning: Molecular Cloning: A Laboratory Manual, Cold Spring Harbor Laboratories, New York, Third Edition 2001).

Deimmunized, Chimeric, Humanized, Synhumanized, Primatized and Human Antibodies or Antigen Binding Fragments The antibodies or antigen binding fragments of the present disclosure may be humanized.

The term "humanized antibody" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized antibodies also include antibodies in which one or more residues of the human protein are modified by one or more amino acid substitutions and/or one or more FR residues of the human antibody are replaced by corresponding non-human residues. Humanized antibodies may also comprise residues which are found in neither the human antibody or in the non-human antibody. Any additional regions of the antibody (e.g., Fc region) are generally human. Humanization can be performed using a method known in the art, for example, U.S. Pat. No. 5,225,539, U.S. Pat. No. 6,054,297, U.S. Pat. No. 7,566,771, or U.S. Pat. No. 5,585,089. The term "humanized antibody" also encompasses a super-humanized antibody, for example, as described in U.S. Pat. No. 7,732,578. A similar meaning will be taken to apply to the term "humanized antigen binding fragment".

The antibodies or antigen binding fragments thereof of the present disclosure may be human antibodies or antigen binding fragments thereof. The term "human antibody" as used herein refers to antibodies having variable and, optionally, constant antibody regions found in humans, for example, in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human antibody will also be considered to include a protein comprising FRs from a human antibody or FRs comprising sequences from a consensus sequence of human FRs and in which one or more of the CDRs are random or semi-random, for example, as described in U.S. Pat. No. 6,300,064 and/or U.S. Pat. No. 6,248,516. A similar meaning will be taken to apply to the term "human antigen binding fragment".

The antibodies or antigen binding fragments thereof of the present disclosure may be synhumanized antibodies or antigen binding fragments thereof. The tem "synhumanized antibody" refers to an antibody prepared by a method described in WO2007/019620. A synhumanized antibody includes a variable region of an antibody, wherein the variable region comprises FRs from a New World primate antibody variable region and CDRs from a non-New World primate antibody variable region.

The antibody or antigen binding fragment thereof of the present disclosure may be primatized. A "primatized antibody" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example an antibody or antigen binding fragment thereof of the disclosure is a chimeric antibody or fragment. The term "chimeric antibody" or "chimeric antigen binding fragment" refers to an antibody or fragment in which one or more of the variable domains is from a particular species (e.g., murine, such as mouse or rat) or belonging to a particular antibody class or subclass, while the remainder of the antibody or fragment is from another species (such as, for example, human or non-human primate) or belonging to another antibody class or subclass. In one example, a chimeric antibody comprising a VH and/or a VL from a non-human antibody (e.g., a murine antibody) and the remaining regions of the antibody are from a human antibody. The production of such chimeric antibodies and antigen binding fragments thereof is known in the art, and may be achieved by standard means (as described, e.g., in U.S. Pat. No. 6,331,415, U.S. Pat. No. 5,807,715, U.S. Pat. No. 4,816,567 and U.S. Pat. No. 4,816,397).

The present disclosure also contemplates a deimmunized antibody or antigen binding fragment thereof, e.g., as described in WO2000/34317 and WO2004/108158. De-immunized antibodies and fragments have one or more epitopes, for example, B cell epitopes or T cell epitopes removed (i.e., mutated) to thereby reduce the likelihood that a subject will raise an immune response against the antibody or protein. For example, an antibody of the disclosure is analyzed to identify one or more B or T cell epitopes and one or more amino acid residues within the epitope is mutated to thereby reduce the immunogenicity of the antibody.

Antibody Fragments
Single-Domain Antibodies

In some examples, an antigen binding fragment of an antibody of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Diabodies, Triabodies, Tetrabodies

In some examples, an antigen binding fragment of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure VL-X-VH or VH-X-VL, wherein X is a linker comprising insufficient residues to permit the VH and VL in a single polypeptide chain to associate (or form an Fv) or is absent, and wherein the VH of one polypeptide chain binds to a VL of the other polypeptide chain to form an antigen binding site, i.e., to form a Fv molecule capable of specifically binding to one or more antigens. The VL and VH can be the same in each polypeptide chain or the VL and VH can be different in each polypeptide chain so as to form a bispecific diabody (i.e., comprising two Fvs having different specificity).

A diabody, triabody, tetrabody, etc., capable of inducing effector activity can be produced using an antigen binding fragment capable of binding to a peptide of the disclosure and an antigen binding fragment capable of binding to a cell surface molecule on an immune cell, for example, a T cell (e.g., CD3).

Single Chain Fv (scFv) Fragments

The skilled artisan will be aware that scFvs comprise VH and VL regions in a single polypeptide chain and a polypeptide linker between the VH and VL which enables the scFv to form the desired structure for antigen binding (i.e., for the VH and VL of the single polypeptide chain to associate with one another to form a Fv). For example, the linker comprises in excess of 12 amino acid residues with (Gly4Ser)3 being one of the more favored linkers for a scFv.

The present disclosure also contemplates a disulfide stabilized Fv (or diFv or dsFv), in which a single cysteine residue is introduced into a FR of VH and a FR of VL and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, for example, by a leucine zipper domain (e.g., derived from Fos or Jun). Alternatively, two scFvs are linked by a peptide linker of sufficient length to permit both scFvs to form and to bind to a peptide or antigen, for example, as described in US 20060263367.

The present disclosure also contemplates a dimeric scFv capable of inducing effector activity. For example, one scFv binds to a peptide of the disclosure and another scFv binds to a cell surface molecule on an immune cell, for example, a T cell (e.g., CD3 or CD19). In one example, the dimeric protein is a combination of a dAb and a scFv. Examples of bispecific antibody fragments capable of inducing effector function are described, for example, in U.S. Pat. No. 7,235,641.

Other Antibodies and Antibody Fragments

The present disclosure also contemplates other antibodies and antibody fragments, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) Fab3 (e.g., as described in EP19930302894).

Exemplary Antibodies or Antigen Binding Fragments

In one example, the antibody or antigen binding fragment thereof is not an—LM1 antibody, variant, or functional fragment as defined in WO 2004/081027 or WO2010/004438.

In one example, the antibody or antigen binding fragment thereof is not:
(i) an antibody or antigen binding fragment thereof comprising a variable heavy chain sequence as shown in SEQ ID NO: 26 or 27,
(ii) an antibody or antigen binding fragment thereof comprising a variable heavy chain sequence as shown in SEQ ID NO:26 or 27 and a variable light chain sequence as shown in SEQ ID NO:28,
(iii) three complementarity determining regions (CDRs) of the amino acid sequence shown in SEQ ID NO:26 or 27, or
(iv) three complementarity determining regions (CDRs) of the amino acid sequence shown in SEQ ID NO:28.

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immuno Globulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer peptide or antigen binding. For example, three loops at one end of the β-sandwich of the $^{10}$Fn3 domain can be engineered to enable an Adnectin to specifically recognize a peptide or antigen. For further details see US 20080139791 or WO 2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to a peptide or antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to a peptide or antigen. The Z domain consists of a three-helical bundle of approximately 58 amino acids. Libraries have been generated by randomization of surface residues. For further details see EP 1641818.

Avimers

In a further example, a compound of the disclosure is an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO 2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target peptides or antigens by randomizing residues in the first α-helix and a β-turn of each repeat. Their binding interface can be increased by increasing the number of modules (a method of affinity maturation). For further details see US 20040132028.

Other Non-Antibody Polypeptides

Other non-antibody proteins comprising binding domains include those based on human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins).

Small Molecules

In another example, a binding molecule is a small molecule. Such a small molecule may be isolated from a library. Chemical small molecule libraries are available commercially or alternatively, may be generated using methods known in the art, such as, for example, those described in U.S. Pat. No. 5,463,564.

Techniques for synthesizing small organic compounds will vary considerably depending upon the compound, however such methods will be known to those skilled in the art.

In one example, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and log P (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Nucleic Acid Aptamers

In another example, a binding molecule is a nucleic acid aptamer (adaptable oligomer). Aptamers are single stranded oligonucleotides or oligonucleotide analogs that are capable of forming a secondary and/or tertiary structure that provides the ability to bind to a particular target such as a peptide of the disclosure, or an antigen comprising said peptide (e.g., NMT55). Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to a peptide of the disclosure, or an antigen comprising said peptide (e.g., NMT55) is selected. An aptamer with increased activity is selected, for example, using SELEX (Sytematic Evolution of Ligands by EXponential enrichment). Suitable methods for producing and/or screening an aptamer library are described, for example, in Elloington and Szostak, Nature 346:818-22, 1990; U.S. Pat. No. 5,270,163; and/or U.S. Pat. No. 5,475,096.

Selection of Compounds that Specifically Bind to Peptides of the Disclosure

Suitable methods for selecting a compound (e.g., an antibody or antigen binding fragment thereof) that specifically binds to a peptide of the disclosure (which comprises an NMT55 epitope or mimotope) are available to those skilled in the art.

For example, a screen may be conducted to identify compounds capable of binding to a peptide of the disclosure.

For example, a phage display library displaying antibody fragments is screened with a peptide of the disclosure to identify proteins that bind thereto. A screening process for immunization of a non-human mammal can also be devised based on the foregoing as can a screening method for identifying other compounds described herein.

In a further example, a peptide of the disclosure or a cell expressing same is contacted with antibody LM1. A library (e.g., a phage display library) is then brought into contact with the LM1 or a cell expressing same or the N-terminal domain thereof or a soluble form thereof and compounds (or phage or cells expressing compounds) that can compete with LM1 for binding selected.

In a still further example, a chimeric protein comprising, for example, a mouse NMT55 in which a peptide of present disclosure (which comprises an NMT55 epitope or mimotope) is substituted for the corresponding mouse sequence. This chimeric protein is then used to immunize mice (which are less likely to induce an immune response against the mouse protein) and/or to screen a library. The resulting compounds (e.g., antibodies) are then screened to identify those that bind to a peptide of the disclosure and not mouse NMT55.

Constant Regions

The present disclosure encompasses compounds (e.g., antibodies and antigen binding fragments thereof) comprising a constant region of an antibody and/or a Fc region of an antibody.

Sequences of constant regions and/or Fc regions useful for producing the immunoglobulins, antibodies or antigen binding fragments of the present disclosure may be obtained from a number of different sources. In some examples, the constant region, Fc or portion thereof of the compound is derived from a human antibody. The constant region, Fc or portion thereof may be derived from any antibody class, including IgA, IgM, IgG, IgD, IgA and IgE, and any antibody isotype, including IgG1, IgG2, IgG3 and IgG4. In one example, the constant region or Fc is human isotype IgG1 or human isotype IgG2 or human isotype IgG3 or a hybrid of any of the foregoing.

In one example, the constant region or Fc region is capable of inducing an effector function. For example, the constant region or Fc region is a human IgG1 or IgG3 Fc region. In another example, the constant region or Fc region is a hybrid of an IgG1 and an IgG2 constant region or Fc region or a hybrid of an IgG1 and an IgG3 constant region or Fc region or a hybrid of an IgG2 and an IgG3 constant region or Fc region. Exemplary hybrids of human IgG1 and IgG2 constant region or Fc regions are described in Chappel et al., 1991.

Methods for determining whether or not a Fc region can induce effector function will be apparent to the skilled artisan and/or described herein.

Effector Function

Suitably, a compound of the disclosure (e.g., an anti-NMT55 antibody or antigen binding fragment thereof) has or displays an effector function that facilitates or enables at least partial depletion, substantial depletion or elimination of NMT55 expressing cells. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

As will be apparent to the skilled artisan based on the description herein, some examples of the present disclosure include a compound (e.g., an antibody or antigen binding fragment thereof) capable of inducing effector function.

For the IgG class of antibodies, some effector functions (e.g., ADCC and ADCP) are governed by engagement of the Fc region with a family of receptors referred to as the Fcγ receptors (FcγRs) which are expressed on a variety of immune cells and/or with complement, for example, C1q (e.g., CDC).

Formation of the Fc/FcγR complex recruits immune cells to sites of bound antigen, typically resulting in signaling and subsequent immune responses. Methods for optimizing the binding affinity of the FcγRs to the antibody Fc region in order to enhance the effector functions, for example, to alter the ADCC activity relative to the "parent" Fc region, are known to persons skilled in the art. These methods can include modification of the Fc region of the antibody to enhance its interaction with relevant Fc receptors and increase its potential to facilitate ADCC and ADCP. Enhancements in ADCC activity have also been described following the modification of the oligosaccharide covalently attached to IgG1 antibodies at the conserved Asn297 in the Fc region.

It will be appreciated by the skilled artisan that in some non-limiting examples, enhancing effector function such as ADCC may be achieved by modification of a compound (e.g., an antibody) which has a normally glycosylated wild-type constant domain, including alteration or removal of glycosylation (see for example WO00/61739) and/or amino acid sequence mutations (see for example WO2008036688).

In one example, the compound binds to NMT55 in such a manner that it is capable of inducing an effector function, such as, ADCC.

In one example, the compound binds to an epitope within NMT55 that permits it to induce an effector function, such as ADCC.

In another example, the compound is capable of binding to NMT55 on a cell in a mammal to thereby induce an effector function, such as ADCC.

For example, the compound remains bound to NMT55 on the surface of a cell for a time sufficient to induce an effector function, such as ADCC. For example, the compound is not internalized too quickly to permit ADCC to be induced.

Alternatively, or in addition, the compound is bound to the NMT55 on the surface of the cell in a manner permitting an immune effector cell to bind to a constant region or Fc region in the compound and induce an effector function, such as ADCC. For example, the Fc region of the compound is exposed in such a manner when the compound is bound to the NMT55 that is capable of interacting with a Fc receptor (e.g., a FcγR) on an immune effector cell. In the context of the present disclosure, the term "immune effector cell" shall be understood to mean any cell that expresses a Fc receptor and that is capable of killing a cell to which it is bound by ADCC or ADCP.

Each of the above paragraphs relating to effector functions of an antibody or antigen binding fragment shall be taken to apply mutatis mutandis to inducing CDC. For example, the compound is bound to the NMT55 on the surface of the cell in a manner permitting complement component C1q to bind to a constant region or Fc region in the compound and induce CDC.

Moreover, each of the above paragraphs relating to effector functions of an antibody or antigen binding fragment shall be taken to apply mutatis mutandis to inducing cell-mediated effector function (e.g., ADCC and/or ADCP) by virtue of a compound other than a Fc region or constant region of an antibody. For example, the cell-mediated effector function is elicited using a compound that binds to NMT55 as described herein and to an immune effector cells (e.g., by virtue of binding to CD19 on NK cells and/or CD4 on T cells).

In one example, the compound is capable of inducing an enhanced level of effector function.

In one example, the level of effector function induced by the constant region or Fc region is enhanced relative to a wild-type constant region or Fc region of an IgG1 antibody or a wild-type constant region or Fc region of an IgG3 antibody.

In another example, the constant region or Fc region is modified to increase the level of effector function it is capable of inducing compared to the constant region or Fc region without the modification. Such modifications can be at the amino acid level and/or the secondary structural level and/or the tertiary structural level and/or to the glycosylation of the constant region or Fc region.

The skilled addressee will appreciate that greater effector function may be manifested in any of a number of ways, for example as a greater level of effect, a more sustained effect or a faster rate of effect.

In one example, the constant region or Fc region comprises one or more amino acid modifications that increase its ability to induce enhanced effector function. In one example, the constant region or Fc region binds with greater affinity to one or more FcγRs. In one example, the constant region or Fc region has an affinity for an FcγR that is more than 1-fold greater than that of a wild-type constant region or Fc region or more than 5-fold greater than that of a wild-type constant region or Fc region or between 5-fold and 300-fold greater than that of a wild-type constant region or Fc region. In one example, the constant region or Fc region comprises at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the constant region or Fc region comprises at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the constant region or Fc region comprises amino acid substitutions selected from the group consisting of V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/I332E, S239Q/V264I/I332E, S239E/V264I/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239D/V264I/I332E, S239D/V264I/S298A/I332E, S239D/V264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/V264T, S239D/A330Y/I332E/K326E, and S239D/A330Y/I332E/K326T, numbered according to the EU index of Kabat.

In another example, the constant region or Fc region binds to FcγRIIIa more efficiently than to FcγRIIb. For example, the constant region or Fc region comprises at least one amino acid substitution at a position selected from the group consisting of: 234, 235, 239, 240, 264, 296, 330, and I332, numbered according to the EU index of Kabat. In one example, the constant region or Fc region comprises at least one amino acid substitution selected from the group consisting of: L234Y, L234I, L235I, S239D, S239E, S239N, S239Q, V240A, V240M, V264I, V264Y, Y296Q, A330L, A330Y, A330I, I332D, and I332E, numbered according to the EU index of Kabat. For example, the constant region or Fc region comprises amino acid substitutions selected from the group consisting of: I332E, V264I/I332E, S239E/I332E, S239Q/I332E, Y296Q, A330L, A330Y, I332D, S239D, S239D/I332E, A330Y/I332E, V264I/A330Y/I332E, A330L/I332E, V264I/A330L/I332E, L234Y, L234I, L235I, V240A, V240M, V264Y, A330I, S239D/A330L/I332E, S239D/S298A/I332E, S239N/S298A/I332E, S239D/V264I/I332E, S239D/V264I/S298A/I332E, and S239D/V264I/A330L/I332E, numbered according to the EU index of Kabat.

In a further example, the constant region or Fc region induces ADCC at a level greater than that mediated by a wild-type constant region or Fc region. For example, the constant region or Fc region induces ADCC at a level that is more than 5-fold or between 5-fold and 1000-fold greater than that induced by a wild-type constant region or Fc region. In one example, the constant region or Fc region comprises at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the constant region or Fc region comprises at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E. K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the constant region or Fc region comprises amino acid substitutions selected from the group consisting of: V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, P L328I/I332E, S239E/V264I/I332E, S239Q/V264I/I332E, S239E/V264I/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239D/V264I/I332E, S239D/V264I/S298A/I332E, S239D/V264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/V264T, S239D/A330Y/I332E/K326E, and S239D/A330Y/I332E/K326T, numbered according to the EU index of Kabat.

In one example, the constant region or Fc region comprises the following amino acid substitutions S239D/I332E, numbered according to the EU index of Kabat. This constant region or Fc region has about 14 fold increase in affinity for FcγRIIIa compared to a wild-type constant region or Fc region and about 3.3 increased ability to induce ADCC compared to a wild-type constant region or Fc region.

In one example, the constant region or Fc region comprises the following amino acid substitutions S239D/A330L/I332E, numbered according to the EU index of Kabat. This constant region or Fc region has about 138 fold increase in affinity for FcγRIIIa compared to a wild-type constant region or Fc region and about 323 increased ability to induce ADCC compared to a wild-type constant region or Fc region.

Additional amino acid substitutions that increase ability of a Fc region to induce effector function are known in the art and/or described, for example, in U.S. Pat. No. 6,737,056 or U.S. Pat. No. 7,317,091.

In one example, the glycosylation of the constant region or Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the constant region or Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some examples, constant regions or Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated Fc regions or constant regions include, expressing the immunoglobulin or antibody in a cell line incapable of expressing α-1,6-fucosyltransferase (FUT8) (e.g., as described in Yumane-Ohnuki et al., 2004), expressing the immunoglobulin or antibody in cells expressing a small interfering RNA against FUT8 (e.g., as described in Mori et al., 2004), expressing the antibody or antigen binding fragment in cells incapable of expressing guanosine diphosphate (GDP)-mannose 4,6-dehydratase (GMD) (e.g., as described in Kanda et al., 2007). The present disclosure also contemplates the use of compounds having a reduced level of fucosylation, e.g., produced using a cell line modified to express β-(1,4)-N-acetylglucosaminyltransferase III (GnT-III) (e.g., as described in Umāna et al., 1999).

In one example, an antibody or antigen binding fragment according to the present disclosure is afucosylated. For example, the immunoglobulin or antibody is produced in a cell (e.g., a mammalian cell, such as a CHO cell) that does not express FUT8.

Other methods include the use of cell lines which inherently produce Fc regions or constant regions or antigen binding fragments capable of inducing enhanced Fc-mediated effector function (e.g. duck embryonic derived stem cells for the production of viral vaccines, WO2008/129058; Recombinant protein production in avian EBX® cells, WO2008/142124).

Compounds (e.g., antibodies or antigen binding fragments) useful in the methods of the present disclosure also include those with bisected oligosaccharides, e.g., in which a biantennary oligosaccharide attached to the constant region or Fc region is bisected by GlcNAc. Such compounds may have reduced fucosylation and/or improved ADCC function. Examples of such compounds are described, e.g., in U.S. Pat. No. 6,602,684 and US20050123546.

Compounds (e.g., antibodies or antigen binding fragments) with at least one galactose residue in the oligosaccharide attached to the constant region or Fc region are also contemplated. Such antibodies or antigen binding fragments may have improved CDC function. Such immunoglobulins are described, for example, in WO1997/30087 and WO1999/22764.

Methods for determining the ability of a compound to induce effector function and known in the art and/or described in more detail herein.

Additional Modifications

The present disclosure also contemplates additional modifications to constant regions or Fc regions of compounds (e.g., antibodies or antigen binding fragments).

For example, constant region of Fc region comprises one or more amino acid substitutions that increase the half-life of the antibody or fragment. For example, the constant region or Fc region comprises one or more amino acid substitutions that increase the affinity of the constant region or Fc region for the neonatal Fc region (FcRn). For example, the constant region or Fc region has increased affinity for FcRn at lower pH, e.g., about pH 6.0, to facilitate Fc/FcRn binding in an endosome. In one example, the constant region or Fc region has increased affinity for FcRn at about pH 6 compared to its affinity at about pH 7.4, which facilitates the re-release of constant region or Fc into blood following cellular recycling. These amino acid substitutions are useful for extending the half life of a Fc containing or constant region containing compound, by reducing clearance from the blood.

Exemplary amino acid substitutions include T250Q and/or M428L according to the EU numbering system of Kabat. Additional or alternative amino acid substitutions are described, for example, in US20070135620.

Protein Production
Recombinant Expression

In one example, a compound as described herein is a polypeptide (e.g., an antibody or antigen binding fragment thereof). In one example, the compound is recombinant.

In the case of a recombinant peptide or polypeptide, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin or antibody protein.

A nucleic acid sequence encoding the peptide or polypeptide may be amplified using the polymerase chain reaction (PCR). The PCR technique is known in the art and is described, for example in U.S. Pat. No. 4,683,195. For example, the sequence of a monoclonal antibody expressed by a hybridoma may be obtained and functional fragments of the antibody may be amplified. For example, whole RNA may be isolated from a hybridoma expressing a tumor-specific monoclonal antibody. cDNA may then be generated from the RNA using reverse transcriptase and the cDNAs which contain the functional fragments of the variable regions of the heavy and light chains may be amplified using PCR. The PCR products may then be purified and cloned into expression vectors. Many standard vectors are available and the selection of the appropriate vector will depend on, for example, the size of the DNA inserted into the vector and the host cell to be transfected with the vector.

Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells. Thus, another example of the disclosure provides an expression construct that comprises an isolated nucleic acid of the disclosure and one or more additional nucleotide sequences. Nucleic acid molecules may be expressed in a variety of standard vectors and host cells. Any promoter that is active in the host cell may be used to express a nucleic acid molecule.

Suitably, the expression construct is in the form of, or comprises genetic components of, a plasmid, bacteriophage, a cosmid, a yeast or bacterial artificial chromosome as are understood in the art. Expression constructs may be suitable for maintenance and propagation of the isolated nucleic acid in bacteria or other host cells, for manipulation by recombinant DNA technology and/or for expression of the nucleic acid or a compound of the disclosure.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding the compound (e.g., derived from the information provided herein), an enhancer element, a promoter, and a transcription termination sequence. Exemplary signal sequences include prokaryotic secretion signals (e.g., pelB, alkaline phosphatase, penicillinase, lpp, or heat-stable enterotoxin II), yeast secretion signals (e.g., invertase leader, $\alpha$ factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-$\alpha$ promoter (EF1), small nuclear RNA promoters (U1a and U1b), $\alpha$-myosin heavy chain promoter, Simian virus 40 promoter (SV40), Rous sarcoma virus promoter (RSV), Adenovirus major late promoter, $\beta$-actin promoter; hybrid regulatory element comprising a CMV enhancer/$\beta$-actin promoter or an immunoglobulin or antibody promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO). For expression of an antibody or a binding fragment thereof in a mammalian cell, use of an immunoglobulin gene promoter is desirable.

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques.

Methods of introducing a vector into a host cell are standard in the art and include, electroporation, use of synthetic lipid polymers, for example, Lipofectin™, use of calcium chloride, and use of DEAE Dextran. Such methods are also described in, for example, Ausubel et al., Current Protocols in Molecular Biology, Wiley Interscience, New York, 2001; and Sambrook et al., Molecular Cloning: A Laboratory Manual, 3rd edition, Cold Spring Harbor Laboratory Press, N.Y., 2001.

The host cells used to produce the compound (e.g., antibody or antigen binding fragment) may be cultured in a variety of media, depending on the cell type used. Commercially available media such as Ham's F10 (Sigma), Minimal Essential Medium ((MEM). (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for purifying a peptide or polypeptide (e.g., an antibody or antigen binding fragment) are known in the art and/or described herein.

Where a peptide or polypeptide is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The peptide or polypeptide prepared from cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbour Laboratory, (1988).

Peptide Synthesis

A peptide is synthesized using a chemical method known to the skilled artisan. For example, synthetic peptides are prepared using known techniques of solid phase, liquid phase, or peptide condensation, or any combination thereof, and can include natural and/or unnatural amino acids Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Nα-amino protected 9-fluorenylmethoxycarbonyl (Fmoc) amino acids described by Carpino and Han, J. Org. Chem., 37:3403-3409, 1972. Both Fmoc and Boc Na-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present disclosure.

A peptide as described herein can also be chemically prepared by other methods such as by the method of simultaneous multiple peptide synthesis. See, e.g., Houghten Proc. Natl. Acad. Sci. USA 82: 5131-5135, 1985 or U.S. Pat. No. 4,631,211.

Nucleic Acid Synthesis

Methods for producing/synthesizing nucleic acid-based compounds of the disclosure lare known in the art. For example, oligonucleotide synthesis is described, in Gait (editor) Oligonucleotide Synthesis: A Practical Approach, IRL Press, Oxford (1984). For example, a probe or primer may be obtained by biological synthesis (e.g. by digestion of a nucleic acid with a restriction endonuclease) or by chemical synthesis. For short sequences (up to about 100 nucleotides) chemical synthesis is desirable.

For longer sequences standard replication methods employed in molecular biology are useful, such as, for example, the use of M13 for single stranded DNA as described by Messing Methods Enzymol, 101: 20-78, 1983.

Other methods for oligonucleotide synthesis include, for example, phosphotriester and phosphodiester methods (Narang, editor, "Synthesis and Applications of DNA and RNA" Academic Press, New York (1987)) and synthesis on a support (Beaucage, et al., 1981) as well as phosphoramidate technique, Caruthers et al., 1988), and others described in Narang (1987), and the references contained therein.

Assaying Activity of Compounds

Compounds of the disclosure are readily screened for biological activity, for example, as described below.

Binding Assays

One form of such an assay is an antigen binding assay, for example, as described in Scopes (In: Protein purification: principles and practice, Third Edition, Springer Verlag, 1994). Such a method generally involves labeling the compound (e.g., an antibody or antigen binding fragment) and contacting it with immobilized peptide of the disclosure or antigen (e.g., NMT55). Following washing to remove non-specific bound protein, the amount of label and, as a consequence, bound compound is detected. Of course, the compound can be immobilized and the peptide or antigen labeled. Panning-type assays, for example, as described herein can also be used.

Determining Competitive Binding

Assays for determining a compound that competitively inhibits binding of an antibody described herein will be apparent to the skilled artisan. For example, the antibody is conjugated to a detectable label, for example, a fluorescent label or a radioactive label. The labeled antibody and the compound are then mixed and contacted with a peptide of the disclosure, antigen comprising said peptide (e.g., NMT55), or cell expressing said peptide or antigen. The level of bound labeled antibody is then determined and compared to the level determined when the labeled antibody is contacted with the peptide of the disclosure, antigen comprising said peptide (e.g., NMT55), or cell expressing said peptide or antigen in the absence of the compound. If the level of labeled antibody is reduced in the presence of the compound compared to the absence of the compound, the compound is considered to competitively inhibit binding of the labeled antibody to the peptide or antigen.

In another example, the compound is permitted to bind to a peptide of the disclosure, antigen comprising said peptide (e.g., NMT55), or cell expressing said peptide or antigen prior to contacting the peptide, antigen, or cell with the labeled antibody. A reduction in the amount of bound labeled antibody in the presence of the compound compared to in the absence of the compound indicates that the compound competitively inhibits binding of the labeled antibody to the peptide or antigen. A reciprocal assay can also be performed using labeled test antibody or antigen binding fragment.

Determining Effector Function

Methods for assessing ADCC activity are known in the art.

In one example, the level of ADCC activity is assessed using a $^{51}$Cr release assay, a europium release assay or a $^{35}$S release assay. In each of these assays, cells expressing NMT55 are cultured with one or more of the recited compounds for a time and under conditions sufficient for the compound to be taken up by the cell. In the case of a $^{35}$S release assay, cells expressing NMT55 can be cultured with $^{35}$S-labeled methionine and/or cysteine for a time sufficient for the labeled amino acids to be incorporated into newly synthesized proteins. Cells are then cultured in the presence or absence of a compound of the disclosure and in the presence of immune effector cells. The amount of $^{51}$Cr, europium and/or $^{35}$S in cell culture medium is then detected, and an increase in the presence of the compound compared to in the absence of the compound indicates that the antibody or antigen binding fragment has effector function. Exemplary publications disclosing assays for assessing the level of ADCC induced by a compound include Hellstrom, et al., 1986 and Bruggemann, et al., 1987.

Other assays for assessing the level of ADCC induced by a compound include ACTI™ nonradioactive cytotoxicity assay for flow cytometry (CellTechnology, Inc. CA, USA) or Cyto-Tox 96® non-radioactive cytotoxicity assay (Promega, Wis., USA).

Alternatively, or additionally, effector function of a compound is assessed by determining its affinity for one or more FcγRs, e.g., as described in U.S. Pat. No. 7,317,091.

C1q binding assays may also be carried out to confirm that the compound is able to bind C1q and may induce CDC. To assess complement activation, a CDC assay may be performed (see, for example, Gazzano-Santoro et al., 1996.

Determining Affinity

Optionally, the dissociation constant (Kd) or association constant (Ka) or equilibrium constant (K$_D$) of a compound for the peptide of the disclosure, or antigen comprising said peptide (e.g., NMT55) is determined. These constants for a compound (e.g., an antibody or antigen binding fragment) are, in one example, measured by a radiolabeled or fluorescently-labeled peptide or antigen binding assay. This assay equilibrates the compound with a minimal concentration of labeled peptide or antigen (e.g., NMT55 or a soluble form thereof) in the presence of a titration series of unlabeled peptide or antigen. Following washing to remove unbound peptide or antigen, the amount of label is determined.

Affinity measurements can be determined by standard methodology for antibody reactions, for example, immunoassays, surface plasmon resonance (SPR) (Rich and Myszka Curr. Opin. Biotechnol 11: 54, 2000; Englebienne Analyst. 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized peptide or antigen (e.g., NMT55 or a soluble form thereof). Exemplary SPR methods are described in 057229619.

Assessing Therapeutic Efficacy

Various in vitro assays are available to assess the ability of a compound of the disclosure to treat a disease or condition described herein.

For example, a compound is assessed for its ability to kill a cell, for example, a cancer cell, such as a breast cancer cell by inducing apoptosis.

"Inducing apoptosis" as used herein, refers to the appearance of characteristics in a cell that are well defined in the art (see, e.g., Wyllie et al., 1999; Kerr et al., 1972). These characteristics include morphological characteristics, such as membrane blebbing, DNA condensation, as well as changes in F-actin content, mitochondrial mass, and membrane potential. The induction of apoptosis may be assayed using a number of methods standard in the art, for example, a cell death ELISA, TUNEL staining, DNA stains, e.g., Hoechst 33258, and staining with various vital dyes such as acridine orange, Mito Tracker Red staining (Molecular Probes, Eugene, Oreg.), and Annexin V staining (Becton Dickinson, N.J.). As used herein"inducing apoptosis" refers to an increase in the number of cells undergoing apoptosis when compared with a control cell population. For instance, the increase of apoptosis may be 10%, 20%, 40%, 50%, or 75%. In desirable embodiments, the induction of apoptosis results in an increase of apoptosis that is 2-fold, 3-fold, 10-fold, or even 100-fold over that seen in a control cell population.

In another example, a compound is assessed for its ability to decrease proliferation of a cell, for example, a cancer cell, such as a breast cancer cell.

Inhibition of cell proliferation may be assayed using a number of methods standard in the art, for example, the MTT cell proliferation assay, BrdU incorporation, and 3H thymidine uptake. Such assays are described, for example, in Ausubel et al., Current Protocols in Molecular Biology, Wiley li1terscience. New York, 2001; and Sambrook et al., Molecular 'losaih: A Laboratoi)) Manual, 3 rd edition, Cold Spring Harbor Laboratory Press, N. Y., 2001.

The inhibition of cell proliferation may be, for example, is 20%, 40%, 50%, or 75%. In preferred embodiments, the inhibition of cell proliferation is 80%, 90%, 95%, or even a complete inhibition of cell proliferation.

Epitopes/Mimotopes

In one embodiment, the present disclosure provides an isolated peptide of about 6 to 50 amino acids comprising an amino acid sequence shown in any one of SEQ ID NOs: 3, 4 or 5.

In another embodiment, the present disclosure provides an isolated peptide consisting of an amino acid sequence shown in any one of SEQ ID NOs: 3, 4 or 5.

SEQ ID NO: 3 represents a minimal PAT-LM1 epitope sequence found in NMT55. SEQ ID NOs: 4 and 5 represent additional PAT-LM1 epitope sequences (mimotopes) found by phage display experiments.

By "isolated" or "purified" is meant separated from other components that naturally accompany it. Typically, a factor is substantially pure when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule in the genome of an organism. Desirably, the factor is at least 75%, more desirably, at least 90% or 95%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al., (Current Protocols in Molecular Biology, Wiley Interscience, New York, 2001). The factor is desirably at least 2, 5, or 10 times as pure as the starting material, as measured using polyacrylamide gel electrophoresis, column chromatography, optical density, HPLC analysis, or Western analysis (Ausubel et al., Current Protocols in Molecular Biology, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

The terms "protein," "polypeptide," and "peptide" are used interchangeably herein. However, the term "peptide" is typically used to refer to relatively short molecules comprising 50 or less, more preferably 25 or less amino acids. The overall length of each peptide defined herein may be, for example, 6 to 50 amino acids, such as 7, 8, 9 10, 11, 12, 13, 14, 15, 16, 17, 18, 19, 20, 25, 30, 35, 40, 45, or 50 amino acids.

A peptide may comprise one or more of the natural amino acids or non-natural amino acids. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodityrosine, and di-isodityrosine are formed post-translationally.

Non-conventional and/or non-natural amino acids include, for example, α-aminobutyric acid, α-amino-α-methylbutyrate, α-methylaminoisobutyrate, α-methyl-γ-aminobutyrate, α-methylcyclohexylalanine, α-methylcyclopentylalanine, α-methyl-α-naphthylalanine, α-methylpenicillamine, α-naphthylalanine, γ-aminobutyric acid, aminocyclopropane-carboxylate, aminoisobutyric acid, aminonorbornyl-carboxylate, cyclohexylalanine, cyclopentylalanine, D-alanine, D-arginine, D-aspartic acid, D-cysteine, D-glutamine, D-glutamic acid, D-histidine, D-isoleucine, D-leucine, D-lysine, D-methionine, D-ornithine, D-phenylalanine, D-proline, D-serine, D-threonine, D-tryptophan, D-tyrosine, D-valine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, D-N-methyllysine, D-N-methylmethionine, D-N-methylornithine, D-N-methylphenylalanine, D-N-methylproline, D-N-methylserine, D-N-methylthreonine, D-N-methyltryptophan, D-N-methyltyrosine, D-N-methylvaline, L-t-butylglycine, L-ethylglycine, L-homophenylalanine, L-methylethylglycine, L-norleucine, L-norvaline, Lα-methylalanine, Lα-methylarginine, Lα-methylasparagine, Lα-methyl aspartate, Lα-methyl-t-butyglycine, Lα-methylcysteine, Lα-methylglutamate, Lα-methylglutamine, Lα-methylhistidine, Lα-methylhomophenylalanine, Lα-methylisoleucine, Lα-methylleucine, L-α-methyllysine, L-α-methylmethionine, L-α-methylnorleucine, L-α-methylnorvaline, L-α-methylornithine, L-α-methylphenylalanine, L-α-methylproline, L-α-methylserine, L-α-methylthreonine, L-α-methyltryptophan, L-α-methyltyrosine, L-α-methylvaline, L-N-methylalanine, L-N-methylarginine, L-N-methylasparagine, L-N-methylaspartic acid, L-N-methylcysteine, L-N-methylglutamine, L-N-methylglutamic acid, L-N-methylhistidine, L-N-methylisoleucine, L-N-methylleucine, L-N-methyllysine, L-N-methylmethionine, L-N-methylnorleucine, L-N-methylnorvaline, L-N-methylornithine, L-N-methylphenylalanine, L-N-methylproline, L-N-methylserine, L-N-methylthreonine, L-N-methyltryptophan, L-N-methyltyrosine, L-N-methylvaline, L-N-methylethylglycine, L-N-methyl-t-butylglycine, L-N-methylhomophenylalanine, L-O-methylserine, L-O-methylhomoserine, N-(4-aminobutyl)glycine, N-(2-aminoethyl)glycine, N-(3-aminopropyl)glycine, N-(2,2-diphenylethyl)glycine, N-(3,3-diphenylpropyl)glycine, N-(3-guanidinopropyl)glycine, N-(1-hydroxyethyl)glycine, N-(3-indolylyethyl)glycine, N-(2-carbamylethyl)glycine, N-(2-carboxyethyl)glycine, N-(1-methylpropyl)glycine N-(2-methylpropyl)glycine, N-(1-methylethyl)glycine, N-(2-methylthioethyl)glycine N-amino-α-methylbutyrate, N-benzylglycine, N-(carbamylmethyl)glycine, N-(carboxymethyl)glycine, N-cyclobutylglycine, N-cycloheptylglycine, N-cyclohexylglycine, N-cyclodecylglycine, N-cyldodecylglycine, N-cyclooctylglycine, N-cyclopropylglycine, N-cycloundecylglycine, N-(hydroxyethyl)glycine, N-(p-hydroxyphenyl)glycine, N-(imidazolylethyl)glycine, N-methyl-γ-aminobutyrate, N-methylaminoisobutyrate, N-methylcyclohexylalanine, N-methylcyclopentylalanine, N-methylglycine. N-methyl-α-naphthylalanine, N-methylpenicillamine, N-(thiomethyl)glycine, penicillamine, N—(N-(3,3-diphenylpropyl)carbamylmethyl)glycine, N—(N-(2,2-diphenylethyl)carbamylmethyl)glycine, and 1-carboxy-1-(2,2-diphenylethylamino)cyclopropane.

In one embodiment, the present disclosure provides an isolated peptide of about 6 to 50 amino acids comprising an amino acid sequence shown in any one of SEQ ID NOs: 3, 4 or 5 having one or more amino acid substitutions.

In another embodiment, the present disclosure provides an isolated peptide consisting of an amino acid sequence shown in any one of SEQ ID NOs: 3, 4 or 5 having one or more amino acid substitutions.

Substitutions may be conservative amino acid substitutions, in which the substituted amino acid has similar structural or chemical properties with the corresponding amino acid in the reference sequence. Alternatively, the substitutions may be non-conservative amino acid substitutions as long as the desired activity is maintained, i.e., the peptide still binds to PAT-LM-1.

By way of example, conservative amino acid substitutions involve substitution of one aliphatic or hydrophobic amino acids, for example, alanine, valine, leucine and isoleucine, with another; substitution of one hydroxyl-containing amino acid, for example, serine and threonine, with another; substitution of one acidic residue, for example, glutamic acid or aspartic acid, with another; replacement of one amide-containing residue, for example, asparagine and glutamine, with another; replacement of one aromatic residue, for example, phenylalanine and tyrosine, with another; replacement of one basic residue, for example, lysine, arginine and histidine, with another; and replacement of one small amino acid, for example, alanine, serine, threonine, methionine, and glycine, with another.

Such conservative substitutions are shown in Table 1. If such substitutions do not result in a change in functional activity, then more substantial changes, denoted exemplary substitutions in Table 1, may be introduced, and the resulting variant analysed for functional activity.

TABLE 1

Amino acid substitutions

| Original residue | Exemplary substitutions | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp; Phe; Thr; Ser | Phe |
| Val (V) | Leu, Ile, Met; Phe; Ala; norleucine | Leu |

Epitope mapping a monoclonal antibody or, in some cases, polyclonal serum, is generally understood to mean the process of deducing the exact region of the antigen or target molecule for which the antibody preparation has the highest affinity. A determinant or epitope of a target generally is understood to mean the portion of an antigen to which the most robust immune response is generated in terms of avidity and selectivity of binding. Polypeptides or other small fragments of an antigen can be used as immunogen (Niman et al, 1983 and U.S. Pat. No. 5,030,565). In some cases, peptides having unrelated sequences or structures can behave as epitopes or "mimotopes" in terms of being able to act as a binding partner for an antibody or compete for binding with the original antigen. Sequence analysis of these peptides can lead to identification of the structural and physicochemical features of the epitope. In numerous cases, epitopic peptides have little or no sequence homology with the original antigenic protein or polypeptide (Geysen et al., 1986). This finding lent support to the concept that, in some cases, antibodies recognized "conformational epitopes" which are only formed in three-dimensional space upon folding and twisting of the linear sequence or because of association with another polypeptide as in heteromultimers. Conformational epitopes are also termed "mimotopes".

The process of epitope mapping provides information about an antigenic molecule, which when linked to information about the biological activity of the antigen or properties altered in the presence of an antibody, provide a means to deduce or understand the biological functions of the target represented by an antigen or epitope and conversely the scope of the possible effects of an antagonistic antibody which prevents normal interaction of that epitope with its naturally occurring cognate ligands.

Given the above mentioned value that epitope mapping provides, it can be seen that the discovery of any cognate ligand for a therapeutic antibody provides not only a novel mimotope that can function as an alternate directed antigen but further provides a significant tool to measure amount and function of that therapeutic antibody.

The peptides of the present disclosure may be made by methods known in the art. They may be manually or synthetically synthesized using methods and devices known in the art (see, e.g., Stewart and Young (1984) Solid Phase Peptide Synthesis, 2 ed. Pierce, Rockford, Ill.). The epitopes or mimotopes may be purified using protein purification techniques known in the art such as reverse phase high-performance liquid chromatography (HPLC), ion-exchange or immunoaffinity chromatography, filtration or size exclusion, or electrophoresis (See, e.g., Olsnes and Pihl (1973); and Scopes (1982) Protein Purification, Springer-Verlag, NY).

Alternatively, the peptides may be made by recombinant DNA techniques known in the art. Thus, polynucleotides that encode the peptides of the present disclosure are contemplated herein.

The peptides of the present disclosure have numerous applications. They may be used as diagnostic tools. For example, the peptides may be used in methods for detecting, diagnosing, or monitoring a cancer in a subject which comprises contacting a peptide of the present disclosure with a sample obtained from a subject and determining whether an antibody in the sample specifically binds the peptide.

The peptides of the present disclosure may alternatively be used as vaccines. For example, the peptides may be formulated in compositions suitable for inducing an immune response when administered to a subject.

The peptides of the present disclosure may alternatively be used as research tools. For example, the peptides may be used to assay, enrich, isolate or purify an antibody by contacting the antibody with a peptide of the disclosure. In one embodiment, the peptides of the present disclosure are used to generate further antibodies or antigen binding fragments thereof towards target antigens. For example, the peptides may be used in phage display experiments to identify further antibodies or antigen binding fragments thereof towards target antigens, such as NMT55. Such methods may be used to identify antibodies or antigen binding fragments thereof may have enhanced desired properties, for example, increased binding affinity, stability or avidity, compared to the PAT-LM1 antibody.

The peptides of the present disclosure may also be used to prepare antibodies by immunizing a suitable subject, for example, rabbit, goat, mouse or other mammal with the epitope or mimotope by methods known in the art. Such antibodies may be produced by methods known in the art, as described above. See also, for example, Coligan (1991) Current Protocols in Immunology, Wiley/Greene, NY; and Harlow and Lane (1989) Antibodies: A Laboratory Manual, Cold Spring Harbor Press, NY; Stites et al., (1986) Basic and Clinical Immunology, 4th ed. Lange Medical Publications, Los Altos, Calif.; Goding (1986) Monoclonal Antibodies:

Principles and Practice, 2d ed. Academic Press, NY; and Kohler & Milstein, 1975. The antibodies may then be used in methods of the disclosure.

Nucleic Acid Encoding for Peptide

In an embodiment, the composition or vaccine of the present disclosure comprises a nucleic acid encoding the peptide. Multiple nucleic acids can be incorporated into the vaccine to produce a polyvalent antigen vaccine. In an embodiment, the vaccine is a DNA vaccine.

DNA vaccination typically involves the direct in vivo introduction of DNA encoding an antigen into, for example, the muscle or skin of the subject for expression of the antigen by the cells of the subject. Once the DNA encoded antigen is processed and presented by the transfected cells, a cellular and/or humoral immune response may be provoked. DNA vaccines are described in U.S. Pat. No. 5,939,400, U.S. Pat. No. 6,110,898, WO 95/20660 and WO 93/19183.

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by DCs. Vectors containing the nucleic acid-based vaccine of the invention may also be introduced into the desired host by other methods known in the art, for example, transfection, electroporation, microinjection, transduction, cell fusion, DEAE dextran, calcium phosphate precipitation, lipofection (lysosome fusion), or a DNA vector transporter.

Formulation of Compositions or Vaccines

In one embodiment, the present disclosure provides a composition or vaccine comprising a peptide of the disclosure or a nucleic acid encoding therefor.

In another embodiment, the present disclosure provides a method of inducing an immune response comprising administering a peptide or nucleic acid encoding therefor, or a composition or vaccine of the present disclosure to a subject.

The peptide or nucleic acid encoding therefor, may be administered by any suitable means that results in a concentration capable of inducing an immune response. The peptide or nucleic acid encoding therefor may be contained in any appropriate amount in any suitable carrier, and is generally present in an amount of 1-95% by weight of the total weight of the composition. The composition may be provided in a dosage form that is suitable for parenteral (e.g., subcutaneous, intravenous, intramuscular, or intraperitoneal) administration route. The composition or vaccine may be formulated according to conventional pharmaceutical practice (see, e.g., Remington: The Science and Practice of Pharmacy (20th ed.). ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The composition or vaccine may be administered parenterally by injection, infusion or implantation (subcutaneous, intravenous, intramuscular, intraperitoneal, or the like) in dosage forms, formulations, or via suitable delivery devices or implants.

A nucleic acid encoding the peptide can be directly delivered to cells by incorporation into a retroviral, adenoviral or other suitable vector, or various other protein-based or lipid-based gene delivery complexes, as well as through use of techniques facilitating the delivery of "naked" polynucleotides (such as electroporation or "gene gun" delivery). Alternatively, the nucleic acid can be introduced into a host cell capable of expressing the protein for delivery. These transfected or transformed cells can then be implanted (alone or in a barrier device), injected or otherwise introduced in an amount effective to express the antigen in a therapeutically effective amount.

In an alternate embodiment, antigen presenting cells, for example macrophages and/or DCs can be contacted in vitro or ex vivo with a composition to effect loading with antigen and then be administered to the subject. In one embodiment, the antigen presenting cells are derived from the subject or an autologous donor and loaded with antigen ex vivo. For example, blood may be taken from the subject or autologous donor and enriched for peripheral blood mononuclear cells (PBMCs) by density gradient centrifugation, followed by adherence to a plastic surface to enrich monocytes. Adherent cells can then be cultured with a cytokine mix to induce differentiation to for example, immature DCs, and the resulting immature DCs can be contacted with the vaccine antigen and mannans or alternatively, transfected with nucleic acid encoding said antigen. Aliquots (for example, cryopreserved aliquots) of the resultant mature/activated dendritic cell preparations (i.e., having upregulated costimulatory molecules CD40, CD80 and CD86) can then be administered to the subject by, for example, intradermal injection(s) on a protocol defined schedule The composition or vaccine of the disclosure may include at least one pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, adjuvants, solvents, surfactants, suspending agents, buffering agents, lubricating agents, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the invention.

The carrier can be any of those conventionally used and is limited only by chemico-physical considerations, such as solubility and lack of reactivity with the active agent, and by the route of administration. Suitable carriers for this invention include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Compounds which may further enhance the immunogenicity or effectiveness of the compositions of the disclosure (also referred to herein as "adjuvants") may also be included therein, or be co-administered therewith. For instance, the compositions may comprise one or more oils (for example, Freund's Complete and Incomplete), saponins, modified saponins, liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, lipid A, wax D from *Mycobacterium*

*tuberculosis*, as well as substances found in *Corynebacterium parvum, Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. Other known immunogenic macromolecules include polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid or glycolipids, lipids or carbohydrates.

In an embodiment of the disclosure, the peptide or nucleic acid encoding therefor, or the composition or vaccine of the disclosure is administered to a subject who has or is at risk of having a proliferative disorder, for example, a neoplasia, cancer, tumor, or metastasis thereof. If the neoplastic or cancerous cells are in direct contact with the blood (e.g., leukemias), or if the tumor is only accessible by the bloodstream, then the intravenous (IV) route may be used. In cases in which tumors grow in confined spaces such as the pleural cavity or the peritoneal cavity, the peptide or nucleic acid encoding therefor, or the composition or vaccine of the disclosure may be directly administered into the cavity rather than into the blood stream. The formulation and preparation of such compositions are well known to those skilled in the art of pharmaceutical formulation. Suitable formulations can be found in Remington: The Science and Practice of Pharmacy, supra.

Methods of Inducing an Immune Response

In one embodiment, the present disclosure provides a method of inducing an immune response comprising administering a peptide or nucleic acid encoding therefor, or composition, or vaccine of the present disclosure to a subject.

A peptide of the present disclosure may be capable of selectively binding an antibody raised against an antigen from which the epitope or mimotope shown in any one of SEQ ID NOs:3, 4, or 5 was obtained. In some embodiments, a peptide of the present disclosure is capable of specifically binding to an antibody from a subject that was produced as an immune response against an antigen, for example, NMT55, expressed by a cancer in the subject.

In one embodiment, the subject is a mammal. In one example, the subject is a human.

In one embodiment, the immune response protects the subject against a proliferative disease.

A "proliferative disease" as used herein, refers to any disorder that results in the abnormal proliferation of a cell. In one embodiment, the proliferative disease is a neoplasia, cancer, tumor, or metastasis thereof. Specific examples of proliferative diseases are various types of neoplasms, such as stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, and adenocarcinoma of the uterus. However, proliferative diseases may also be the result of the cell becoming infected with a transforming virus.

Exemplary cancers amenable to the methods of the current disclosure include, but are not limited to, colorectal cancer, ovarian carcinoma, squamous cell lung carcinoma, small cell lung carcinoma, lobular and ductal mammary carcinomas, melanoma, breast cancer, lung cancer, such as lung adenocarcinomas, gastric cancer, pancreatic cancer, such as pancreatic adenocarcinomas, glioma, sarcomas, gastrointestinal cancer, brain tumor, esophageal cancer, such as esophagial squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias.

In one embodiment, the method further comprises administering to the subject an anti-cell proliferative or immune-enhancing treatment or therapy.

The compositions and methods described herein can be combined with any other treatment or therapy that provides a desired effect. In particular, treatments and therapies that have been characterized as having an anti-cell proliferative activity or function are applicable. Exemplary treatments and therapies include anti-cell proliferative or immune enhancing agents or drugs.

As used here, the term "immune enhancing," when used in reference to a treatment, therapy, agent or drug means that the treatment, therapy, agent or drug provides an increase, stimulation, induction or promotion of an immune response, humoral or cell-mediated. Such therapies can enhance immune response generally, or enhance immune response to a specific target, for example, a cell proliferative or cellular hyperproliferative disorder such as a neoplasia, cancer, tumor, or metastasis thereof.

Specific non-limiting examples of immune enhancing agents include antibody, cell growth factors, cell survival factors, cell differentiative factors, cytokines and chemokines. Additional examples of immune enhancing agents and treatments include immune cells such as lymphocytes, plasma cells, macrophages, dendritic cells, NK cells and B-cells that either express antibody against the cell proliferative disorder or otherwise are likely to mount an immune response against the cell proliferative disorder. Cytokines that enhance or stimulate immunogenicity include IL-2, IL-1α, IL-1, IL-3, IL-6, IL-7, granulocyte-macrophage-colony stimulating factor (GMCSF), IFN-γ, IL-12, TNF-α, and TNF-β, which are also non-limiting examples of immune enhancing agents. Chemokines including MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, PARC, TARC, LARC/MIP-3α, CKβ, CKβ6, CKβ7, CKβ8, CKβ9, CKβ11, CKβ12, C10, IL-8, ENA-78, GROα, GROβ, GCP-2, PBP/CTAPIIIβ-TG/NAP-2, Mig, PBSF/SDF-1, and lymphotactin are further non-limiting examples of immune enhancing agents.

The treatments and therapies can be performed prior to, substantially contemporaneously with any other methods of the disclosure, for example, an anti-cell proliferative or anti-cellular hyperproliferative disorder (e.g., a neoplasia, cancer, tumor, or metastasis thereof). The present disclosure therefore provides combination methods in which any of the peptides of the disclosure are used in a combination with any therapeutic regimen, treatment protocol or composition, such as an anti-cell proliferative protocol, agent or drug set forth herein or known in the art.

As used herein, an "anti-cell proliferative," "anti-neoplastic," "antitumor," or "anti-cancer" treatment, therapy, activity or effect means any therapy, treatment regimen, agent, drug, protocol or process that is useful in treating pathologies, adverse symptoms or complications associated with or caused by abnormal or undesirable cell proliferation (cell hyperproliferation), a cellular hyperproliferative disorder, neoplasia, cancer, tumor, or metastasis thereof. Particular therapies, treatment regimens, agents, drugs, protocol or processes can inhibit, decrease, slow, reduce, delay, or prevent cell proliferation, cell growth, cellular hyperproliferation, neoplastic, tumor, or cancer (malignant) growth, proliferation, survival or metastasis. Such treatments, therapies, regimens, protocols, agents and drugs, can operate by disrupting, reducing, inhibiting or delaying cell cycle progression or cell proliferation or growth; increasing, stimulating or enhancing cell apoptosis, lysis or death; inhibiting nucleic acid or protein synthesis or metabolism; reducing, decreasing, inhibiting or delaying cell division; or decreasing, reducing or inhibiting cell survival, or production or utilization of a cell survival factor, growth factor or signaling pathway (extracellular or intracellular).

Examples of anti-cell proliferative treatments and therapies include chemotherapy, immunotherapy, radiotherapy (ionizing or chemical), local or regional thermal (hyperthermia) therapy and surgical resection. Specific non-limiting classes of anti-cell proliferative agents and drugs include alkylating agents, anti-metabolites, plant extracts, plant alkaloids, nitrosoureas, hormones (steroids), nucleoside and nucleotide analogues. Specific non-limiting examples of microbial toxins include bacterial cholera toxin, pertussis toxin, anthrax toxin, diphtheria toxin, and plant toxin ricin. Specific examples of drugs include cyclophosphamide, azathioprine, cyclosporin A, melphalan, chlorambucil, mechlorethamine, busulphan, methotrexate, 6-mercaptopurine, thioguanine, 5-fluorouracil, 5-fluorouridine, cytosine arabinoside, 6-thioguanine, 6-mercatopurine, AZT, 5-azacytidine (5-AZC) and 5-azacytidine related compounds, pentostatine, gemcitabine, cytarabine, bleomycin, actinomycin D, dactinomycin, mithramycin, mitomycin C, carmustine, calicheamicin, lomustine, semustine, streptozotocin, teniposide, etoposide, hydroxyurea, nitrosourea, cisplatin, carboplatin, levamisole, ifosfamide, mitotane, mitoxantrone, procarbazine, dacarbazine, taxol, vinblastine, vincristine, vindesine, doxorubicin, daunorubicin, epirubicin, idarubicin, daunomycin and dibromomannitol. Specific non-limiting examples of hormones include prednisone, prednisolone, diethyl stilbesterol, fluoxymesterone, flutamide, leuprolide, toremifene, triamcinolone, zoladex, and gonatrophin releasing hormone antagonists.

Radiotherapy includes internal or external delivery to a subject. For example, alpha, beta, gamma and X-rays can administered to the subject externally without the subject internalizing or otherwise physically contacting the radioisotope. Specific examples of X-ray dosages range from daily doses of 50 to 200 roentgens for prolonged periods of time (3 to 5/week), to single doses of 2000 to 6000 roentgens. Dosages vary widely, and depend on duration of exposure, the half-life of the isotope, the type of radiation emitted, the cell type and location treated and the progressive stage of the disease. Specific non-limiting examples of radionuclides include, for example, 47Sc 67Cu, 72Se. 88Y, 90Sr, 90Y, 97Ru, 99Tc, 105Rh, 111In, 125I, 131I, 149Tb, 153Sm, 186Re, 188Re, 194Os, 203Pb, 211At, 212Bi5 213Bi, 212Pb, 223Ra, 225Ac, 227Ac, and 228Th.

Antibodies that bind to tumor cells are a particular example of an anti-cell proliferative treatment or therapy. Anti-tumor antibodies include, for example, M195 antibody which binds to leukemia cell CD33 antigen (U.S. Pat. No. 6,599,505); monoclonal antibody DS6 which binds to ovarian carcinoma CA6 tumor-associated antigen (U.S. Pat. No. 6,596,503); human IBD12 monoclonal antibody which binds to epithelial cell surface H antigen (U.S. Pat. No. 4,814,275); and BR96 antibody which binds to Lex carbohydrate epitope expressed by colon, breast, ovary, and lung carcinomas. Additional anti-tumor antibodies that can be employed include, for example, Herceptin (anti-Her-2 neu antibody), Rituxan®, Zevalin, Bevacizumab (Avastin), Bexxar, Campath®, Oncolym, 17-1A (Edrecolomab), 3F8 (anti-neuroblastoma antibody), MDX-CTLA4, IMC-C225 (Cetuximab) and Mylotarg.

As used here, the term "immune enhancing," when used in reference to a treatment, therapy, agent or drug means that the treatment, therapy, agent or drug provides an increase, stimulation, induction or promotion of an immune response, humoral or cell-mediated. Such therapies can enhance immune response generally, or enhance immune response to a specific target, for example, a cell proliferative or cellular hyperproliferative disorder such as a neoplasia, cancer, tumor, or metastasis thereof.

Specific non-limiting examples of immune enhancing agents include antibody, cell growth factors, cell survival factors, cell differentiative factors, cytokines, interferons and chemokines. Additional examples of immune enhancing agents and treatments include immune cells such as lymphocytes, plasma cells, macrophages, dendritic cells, NK cells and B-cells that either express antibody against the cell proliferative disorder or otherwise are likely to mount an immune response against the cell proliferative disorder. Cytokines that enhance or stimulate immunogenicity include IL-2, IL-1α, IL-1β, IL-3, IL-6, IL-7, granulocyte-macrophage-colony stimulating factor (GMCSF), IFN-γ, IL-12, TNF-α, and TNFβ, which are also non-limiting examples of immune enhancing agents. Chemokines including MEP-1α, MIP-1β, RANTES, SDF-I, MCP-I, MCP-2, MCP-3, MCP-4, eotaxin, eotaxin-2, ATAC, HCC-I, HCC-2, HCC-3, PARC. TARC, LARC/MIP-3α, CKβ, CKβ6, CKβ7, CKβ8, CKβ9, CKβ11, CKβ12, ClO, IL-8, ENA-78. GROα, GROβ, GCP-2, PBP/CTAPIIIβ-TG/NAP-2, Mig, PBSF/SDF-1, and lymphotactin are further non-limiting examples of immune enhancing agents.

Methods of Assaying, Enriching, Isolating or Purifying Antibodies Against a Tumour Associated Antigen or a B Cell Secreting the Antibody In one embodiment, the present disclosure provides a method for assaying, enriching, isolating or purifying at least one antibody or antigen binding fragment thereof which comprises contacting the antibody or antigen binding fragment thereof with a peptide of the present disclosure.

The terms "assaying" and "measuring" and grammatical variations thereof are used interchangeably herein and refer to either qualitative or quantitative determinations, or both qualitative and quantitative determinations. When the terms are used in reference to binding, any means of assessing the relative amount, affinity or specificity of binding is contemplated, including the various methods set forth herein and known in the art. For example, antibody binding can be assayed or measured by an ELISA assay, Western blot, or immunoprecipitation assay.

The term "contacting," when used in reference to a composition comprising a polypeptide (e.g., antibody), material, sample, or treatment, means a direct or indirect interaction between the composition (e.g., polypeptide such as an antibody) and the other referenced entity. A particular example of direct interaction is binding. A particular example of an indirect interaction is where the composition acts upon an intermediary molecule, which in turn acts upon the referenced entity. Thus, for example, contacting a cell (e.g., that comprises a cellular hyperproliferative disorder) with an antibody includes allowing the antibody to bind to the cell, or allowing the antibody to act upon an intermediary (e.g., antigen) that in turn acts upon the cell.

In one embodiment, the peptides of the present disclosure are used to generate further antibodies towards target antigens. For example, the peptides of the disclosure may be used in phage display experiments to identify further antibodies or antigen binding fragments thereof towards target antigens, such as NMT55. Such methods may be used to identify antibodies or antigen binding fragments thereof that may have enhanced desired properties, for example, increased binding affinity, stability or avidity. Additional non-limiting particular methods of antibody and functional fragment screening and selection include phage display, protein-mRNA link via ribosome and mRNA display, display on yeast, bacteria, mammalian cells or retroviruses, microbead via in vitro compartmentalization, protein-DNA display, growth selection via yeast 2-hybrid, protein fragment complementation (Hoogenboom, 2005).

Methods for Detecting, Diagnosing or Monitoring a Neoplasm. Cancer, or Tumor, or Metastasis Thereof The present disclosure provides a method for detecting, diagnosing, or monitoring a neoplasia, cancer, or tumor, or metastasis thereof in a subject such as a mammal, preferably a human patient. Typically, any neoplasia, cancer, or tumor, or metastasis thereof which expresses NMT55.

In one embodiment, the present disclosure provides a method for detecting, diagnosing, or monitoring a neoplasia, cancer, or tumor, or metastasis thereof in a subject which comprises administering a peptide of the present disclosure to the subject or, alternatively, contacting a peptide of the present disclosure with a sample obtained from the subject and determining whether an antibody in the subject or sample specifically binds the peptide.

In another embodiment, the present disclosure provides a method for detecting, diagnosing, or monitoring a neoplasia, cancer, or tumor, or metastasis thereof in a subject which comprises administering a compound of the present disclosure to the subject or contacting a compound of the present disclosure with a sample obtained from the subject and determining whether the compound specifically binds cells in the subject or sample.

Compounds (e.g., antibodies or antigen binding fragments thereof) that specifically bind the peptides of the present disclosure may be contacted with a biological tissue or sample, in vivo, ex vivo, or in vitro, to determine whether the biological tissue or sample is neoplastic or cancerous, i.e., comprises a cell that expresses an antigen that is specifically bound by the compound. Alternatively, peptides of the present disclosure may be contacted with a biological tissue or sample, in vivo, ex vivo, or in vitro, to determine whether the biological tissue or sample contains antibodies that specifically bind the peptide, thereby indicating the subject suffers from a neoplasm, cancer, tumor, or metastasis thereof.

If desired, the peptide or compound may be linked to a detectable agent to facilitate the purification of the peptide or compound as well as the detecting, diagnosis, or monitoring of cancer in a subject in need thereof. The selection of a suitable detectable agent will depend on the intended use of the peptide or compound and will be apparent to those of ordinary skill in the art. Detectable agents according to the claimed disclosure include, for example, protein purification tags, cytotoxins, enzymes, paramagnetic labels, enzyme substrates, co-factors, enzyme inhibitors, dyes, radionuclides, chemiluminescent labels, fluorescent markers, growth inhibitors, and biotin, as outlined above.

A protein purification tag may be conjugated to the peptide or compound to facilitate isolation of the peptide. Examples of tags that can be used include His-tags, HA-tags, FLAG®-tags, and c-Myc tags. An enzymatic or chemical cleavage site may be engineered between the peptide or compound and the tag moiety so that the tag can be removed following purification. Suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Examples of suitable radioisotopic labels include H, I, I, P, S, and C. Desirably, the radioisotope will emit in the 10-5,000 key range, more desirably 100-500 key. Paramagnetic isotopes may also be conjugated to the peptide or compound and used in vivo for the diagnosis and treatment of cancer.

The use of such conjugated peptides or compounds may be for in vivo nuclear magnetic resonance imaging. Such a method has previously been described (see, for example, Schaefer et al., 1989; Shreve et al., 1986; Wolf, 1984; Wesbey et al., 1984; and Runge et al., 1984). Alternatively, the radiolabeled compound (e.g., antibody or antigen binding fragment thereof) may also be used in radioimmunoguided surgery (RIGS), which involves the surgical removal of any tissue the labeled compound binds to. Thus, the labeled compound guides the surgeon towards neoplastic or cancerous tissue by distinguishing it from non-neoplastic or non-cancerous tissue.

Radiolabels useful for tumor imaging are preferably short-lived radioisotopes. Various radioactive metals with half-lives ranging from 1 hour to 11.4 days are available for conjugation to antibodies, such as scandium-47 (3.4 days), gallium-67 (2.8 days), gallium-68 (68 minutes), technetium-99m (6 hours), indium-I11(3.2 days), and radium-223 (11.4 days), of which gallium-67, technetium-99m, and indium-111 are preferable for gamma camera imaging, gallium-68 is preferable for positron emission tomography, and scandium-47 and radium-223 (and other alpha-emitting radionuclides) are preferable for tumor therapy.

Examples of suitable fluorescent markers include fluorescein, isothiocyalate, rhodamine, phycoerythrin, phycocyanin, allophycocyanin, ophthaldehyde, and fluorescamine. Examples of chemiluminescent markers include a luminal label, isoluminal label, aromatic acridinium ester label, imidazole label, acridinium salt label, oxalate ester label, luciferin label, luciferase label, and aequorin label. Those of ordinary skill in the art would know of other suitable labels, which maybe employed in accordance with the present disclosure. Conjugation of these detectable agents to the peptides or compounds of the disclosure, can be accomplished using standard techniques commonly known in the art. Typical antibody conjugation techniques are described by Kennedy et al., 1976 and Schurs et al., 1977 and include, for example, the glutaraldehyde method, the periodate method, the dimaleimide method, the m-maleimidobenzyl-N-hydroxy-succinimide ester method. Antibodies may be radiolabeled by any of several techniques known to the art, described, for example, in U.S. Pat. No. 4,444,744.

In all aspects of the present disclosure, it is understood that mixtures of different or the same labeled compounds (e.g., antibodies or antigen binding fragments thereof) specific to different antigens or different peptides of the same or different antigens associated with the same or different neoplasm, cancer, tumor or neoplasm, cancer, tumor cell types may be used. Such a combination may enhance detection, localization and/or therapy in certain cases, and can also increase the range of a broad screen for more than one neoplasm or type of neoplasm.

The compounds (e.g., antibodies or antigen binding fragments thereof) of the disclosure are particularly useful since they are specific to neoplasms, cancers, or tumors or neoplastic or cancerous cells, but not normal cells or tissues. Accordingly, in an embodiment, the compounds of the disclosure can bind to neoplastic or cancerous cells within a tumor, but not the normal surrounding tissue, thus allowing the detection, the treatment, or both, of a tumor in a mammal. For instance, one may use a an antibody or antigen binding fragment thereof of the disclosure to determine if a biopsy removed the entire tumor by verifying that no cells bound by the antibody or antigen binding fragment thereof remain in the patient or, by verifying that the tumor removed from the patient is entirely surrounded by cells that are not bound by the antibody or antigen binding fragment thereof.

It is understood that to improve the sensitivity of detection, multiple neoplastic or cancerous markers may be assayed within a given sample or individual. Thus, compounds such as antibodies or antigen binding fragments thereof specific for, different antigens, may be combined within a single assay, or in multiple assays. The selection of markers may be based on routine experiments to determine combinations that results in optimal sensitivity.

In Vitro Detection of a Neoplasm, Cancer or Tumor, or Metastasis Thereof

In general, the diagnosis of a neoplasia, cancer, or tumor, or metastasis thereof in a mammal involves obtaining a biological sample from the mammal (e.g., human patient), contacting such sample with a peptide or compound of the present disclosure, detecting in the sample the level of reactivity or binding of 1) antibodies in the sample to the peptide, relative to a control sample, which corresponds to non-neoplastic or non-cancerous sample derived from a healthy subject 2) the compound to neoplastic or cancerous cells relative to a control sample, which corresponds to non-neoplastic or cancerous cells derived from healthy tissue from the subject in which the cancer is being diagnosed or from a healthy subject. Thus, the methods of this disclosure are particularly useful for the detection of early stage neoplasms, cancers, or tumors, or metastases thereof, which are otherwise undetectable.

In addition to diagnosing a neoplasia, cancer, or tumor, or metastasis thereof in a patient, the methods of this disclosure may also be used to monitor progression of a neoplasia, cancer or tumor, or metastasis thereof in a subject. The peptides described herein therefore may be used as markers for the progression of a neoplasia, cancer, or tumor, or metastasis thereof. For this purpose, the assays described below, which are used for the diagnosis of a neoplasia, cancer, or tumor, or metastasis thereof, may be performed over time, and the change in the level of reactive peptides or compounds evaluated.

For example, the assays may be performed every 24-72 hours for a period of 6 months to 1 year, and thereafter performed as needed. In general, a neoplasia, cancer, or tumor, or metastasis thereof, is progressing in those patients in whom the level of bound compound (e.g., antibody or an antigen binding fragment thereof) detected increases over time, in contrast, the neoplasia, cancer, or tumor, or metastasis thereof, is not progressing when the level of bound compound either remains constant or decreases with time.

Alternatively, as is noted above, the compounds of the disclosure may also be used to determine the presence of neoplastic or cancerous cells in the subject following tumor resection by surgical intervention to determine whether the tumor has been completely removed from the subject.

Desirably, the peptide or compound is linked to a detectable agent, which facilitates detection, or measurement of peptide or compound reactivity. The biological sample is any biological material, which may contain neoplastic or cancerous cells or antibodies to NMT55, and include, for example, blood, saliva, tissue, serum, mucus, sputum, urine, or tears. The biological sample may also be a tissue section, which may be fixed tissue, fresh tissue, or frozen tissues. A neoplasm is detected or diagnosed in the subject from which the sample was obtained if there is an increase in the level of reactivity of the peptide or compound (e.g., antibody of antigen binding fragment thereof) with the biological sample over the control sample. Such increase is at least 10%, 20%, 30%, 40%, 50%, or more than 50% over control levels. The level of binding or reactivity can be determined by any method known in the art and is described in further detail below.

In Vitro Diagnostic Assays

The diagnosis of neoplasms, cancer, tumors, or metastases thereof using a peptide or compound of the disclosure may be performed by any method known to those of ordinary skill in the art for using a binding agent to detect antibodies or peptide markers in a sample (see, e.g., Harlow and Lane, Using Antibodies: A Laboratory Manual, Cold Spring Harbor Laboratory Press, N.Y., 1999).

For example, the peptide or compound may be used for enzyme-linked immunosorbent assay (ELISA), Western blotting or in situ detection of tumor cells in a tissue sample. For example, the ELISA assay typically involves the use of the compound, such as an antibody, immobilized on a solid support to bind to the tumor cells in the biological sample. The bound tumor cell may then be detected using a detection reagent that contains a reporter group and that specifically binds to the antibody/tumor cell complex. Such detection reagents include, for example, any binding agent that specifically binds to the antibody, such as an anti-immunoglobulin, protein G, protein A, or a lectin. Alternatively, a competitive assay may be utilized, in which the compound is an antibody and in which the antigens, to which the antibody is specific to is labeled with a reporter group and allowed to bind to the immobilized antibody after incubation of the antibody with the biological sample. The extent to which components of the sample inhibit the binding of the labeled antigens to the antibody is indicative of the reactivity of the sample with the immobilized antibody. In another example, the ELISA assay involves the use of a peptide of the disclosure, immobilized on a solid support to bind to the antibodies (e.g., anti-NMT55 antibodies) in the biological sample. The bound antibody may then be detected using a detection reagent that contains a reporter group and that specifically binds to the antibody/peptide complex. Such detection reagents include, for example, any binding agent that specifically binds to the antibody, such as an anti-Fc-receptor antibody.

Diagnosis of a neoplasm in a patient may also be determined by a two-antibody sandwich assay. This assay may be performed by first contacting an antibody that has been immobilized on a solid support, commonly the well of a microtiter plate, with the sample, such that polypeptides (e.g., NMT55 or cell expressing same) within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group. For example, to determine the presence or absence of a neoplasm, such as colorectal adenocarcinoma, the signal detected from the reporter group that remains bound to the solid support is generally compared to a signal that corresponds to a predetermined cut-off value. The cut-off value for the detection of a neoplasm is the average mean signal obtained when the antibody is incubated with samples from patients without a neoplasm. The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin maybe detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

The compounds (e.g., antibodies or antigen binding fragments thereof) of the present disclosure may also be employed histologically for in situ detection or quantitative determination of tumor cells, for example, by immunofluorescence or immunoelectron microscopy. In situ detection or determination may be accomplished by removing a tissue specimen from a patient and allowing a labeled antibody to bind to any tumor cell in the specimen. Using such a procedure not only allows the detection of neoplastic cells in a sample, but also allows for the determination of their spatial distribution. As another example, the biological sample can be a smear of biological material containing neoplastic cells on a slide, and the detection of neoplastic cells in the biological material is achieved by examining the smear with a microscope.

In Vivo Detection of a Neoplasm, Cancer, or Tumor, or Metastasis Thereof

Alternatively, a peptide of the disclosure may also be used in vivo for detecting and, possibly, localizing a neoplasm. Such a method may involve injecting a mammal, desirably a human subject, parenterally with a peptide or compound of the disclosure which has been labeled with a detectable agent. For example, the peptide or compound can be radiolabeled with a pharmacologically inert radioisotope and administered to the patient. The activity of the radioisotope can be detected in the mammal using a photoscanning device, and an increase in activity relative to a control reflects the detection and possibly, localization of a neoplasm, cancer, or tumor, or metastasis thereof.

Unless otherwise defined, all technical and scientific terms used herein have the same meaning as commonly understood by one of ordinary skill in the art to which this disclosure relates. Although methods and materials similar or equivalent to those described herein can be used in the practice or testing of the disclosure, suitable methods and materials are described herein.

The present disclosure is described further in the following non-limiting examples.

Example 1

Mapping the PAT-LM1 Epitope

The PAT-LM1 antibody was found previously to recognise NMT55 as its target (see WO 2010/004438). This example describes how scans of overlapping fragments derived from the amino acid sequence of the PAT-LM1 antigen (human NMT55) were used for epitope mapping. In these experiments, the C-terminus of NMT55 was truncated and binding to PAT-LM1 determined by Western blot to find the region where the epitope was located.

1.1 Materials and Methods

Cloning and Expression of NMT55 Subfragments for PAT-LM1 Epitope Mapping

PCR primers were generated to different segments of the C-terminus of NMT55 and amplified with the forward primer encompassing the N-terminus of NMT55, as outlined in FIG. 1. Subsequently, various nmt-55 isoforms shortened at the C-terminal region were cloned.

Primers, used to amplify NMT55 subfragments for epitope mapping were as follows:

```
Nono-Kozak-For:
                                    (SEQ ID NO: 7)
GCCACCATGCAGAGTAATAAAACTTTTAAC;

Nono-290AA-Rev:
                                    (SEQ ID NO: 8)
TTACTTGATGTTGCGGTCCACTTG;

Nono-310AA-Rev:
                                    (SEQ ID NO: 9)
TTACATGACCTGGTGCTCATGGCG;

Nono-330AA-Rev:
                                    (SEQ ID NO: 10)
TTAGTGCAGCTCTTCCATCCTCCG;

Nono-350AA-Rev:
                                    (SEQ ID NO: 11)
TTAGCGCCTGCGCTCTTCCTCCTG;

Nono-370AA-Rev:
                                    (SEQ ID NO: 12)
TTAGAATCCTTCCTGCTGTCGCCG;

Nono-390AA-Rev:
                                    (SEQ ID NO: 13)
TTATCCCATAGCCATCTGACCCAT;

Nono-410AA-Rev:
                                    (SEQ ID NO: 14)
TTAGGTACCAGCTGGCACAGGAGC;

Nono-430AA-Rev:
                                    (SEQ ID NO: 15)
TTATGGTGGGGTCAATCCCAAAGT;

Nono-450AA-Rev:
                                    (SEQ ID NO: 16)
TTAAGTTCCACCAATTGCCCCAAT;

Nono-292AA-Rev:
                                    (SEQ ID NO: 17)
TCAAGCCTCCTTGATGTTGCGGTC;

Nono-294AA-Rev:
                                    (SEQ ID NO: 18)
TCACTCACGAGCCTCCTTGATGTT;

Nono-296AA-Rev:
                                    (SEQ ID NO: 19)
TCACAGCTTCTCACGAGCCTCCTT;

Nono-298AA-Rev:
                                    (SEQ ID NO: 20)
TCACATCTCCAGCTTCTCACGAGC;

Nono-300AA-Rev:
                                    (SEQ ID NO: 21)
TCACATCTCCATCTCCAGCTTCTC;
```

-continued

```
Nono-302AA-Rev:
                                        (SEQ ID NO: 22)
TCAAGCTTCCATCTCCATCTCCAG;

Nono-304AA-Rev:
                                        (SEQ ID NO: 23)
TCAGCGTGCAGCTTCCATCTCCAT;

Nono-306AA-Rev:
                                        (SEQ ID NO: 24)
TCACTCATGGCGTGCAGCTTCCAT;

Nono-308AA-Rev:
                                        (SEQ ID NO: 25)
TCACTGGTGCTCATGGCGTGCAGC.
```

Figure 3:
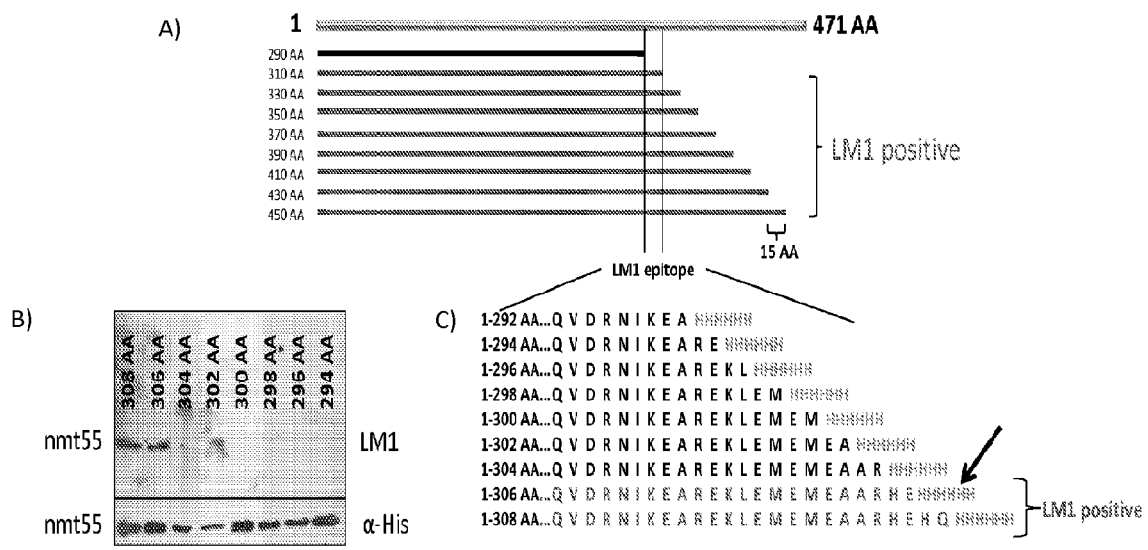
FIG. 3 shows the strategy used for fine mapping the PAT-LM1 epitope on NMT55 (A and C). Panel C provides the amino acid sequences of the peptides screened (SEQ ID NOS:29-37). B) Western blots show that the PAT-LM1 epitope lies between amino acids 292-306 of NMT55.

Using these primers, PCR reactions were performed on NMT55 full length sequence as template to amplify the desired fragments of NMT55. The PCR protocol was about 98° C. for about 5 seconds, about 58° C. for about 5 seconds and about 72° C. for about 10-20 seconds for about 35 cycles. The PCR products were subcloned into the TA cloning vector pEXP5-CT (Invitrogen) and the sequences were confirmed. Expression of overlapping NMT55 proteins were performed in BL21 (*Escherichia coli*) based on Invitrogen expression manual (pEXP5-CT/Topo TA expression Kit).
SDS-PAGE Samples were applied to about a 10% SDS-PAGE after addition of about 15 µl Loading buffer to about 35 µl of lysed cells. About 14 µl samples were loaded per lane, and electrophoresed for about 45 minutes at 40 mA.
Western Blot Gels were blotted in a wet blotting chamber (BioRad) on a PVDF-membrane (Millipore) for about 1 hour at 350 mA. Blots were blocked in about 5% dry milk in PBS-Tween for about one hour. First antibodies anti-His (1:1000) were applied for about 1 hour in about 5% dry milk in PBS-Tween. PAT-LM1 (about 40 µg/ml) was applied for about 2 hours. Blots were washed with PBS-Tween three times for about 5 minutes and Peroxidase-coupled secondary antibody was applied for about one hour. Blots were washed about 3 times for about 15 minutes and were developed with Pierce ECL Super Signal West Pico solutions.
1.2 Results
Initial PAT-LM1 Epitope Mapping The results of the initial epitope mapping experiments are shown in FIG. 2. A fragment comprising amino acids 290-471 of NMT55 was identified as being PAT-LM1 positive (i.e., showed PAT-LM1 binding). Subcloning of NMT55 into ten 15 amino acid reduced fragments was performed as outlined above. A subfragment consisting of amino acids 1-310 of NMT55 was identified as being the last PAT-LM1 positive construct (see FIGS. 2A and B). Thus, it was concluded that the PAT-LM1 epitope mapped between 290-310 amino acids of NMT55.
Fine Mapping the PAT-LM1 Epitope For fine mapping of the PAT-LM1 epitope C-terminus, NMT55 fragments comprising amino acids 290-310 of NMT55 were divided into ten subfragments with a resolution of two amino acids and binding to PAT-LM1 determined by Western blot. The results of these fine mapping experiments are shown in FIG. 3. The PAT-LM1 epitope was determined to lie between amino acids 292-306 of NMT55 (i.e. AREKLE-MEMEAARHE (SEQ ID NO: 2); see FIGS. 3A and B).

Figure 4:
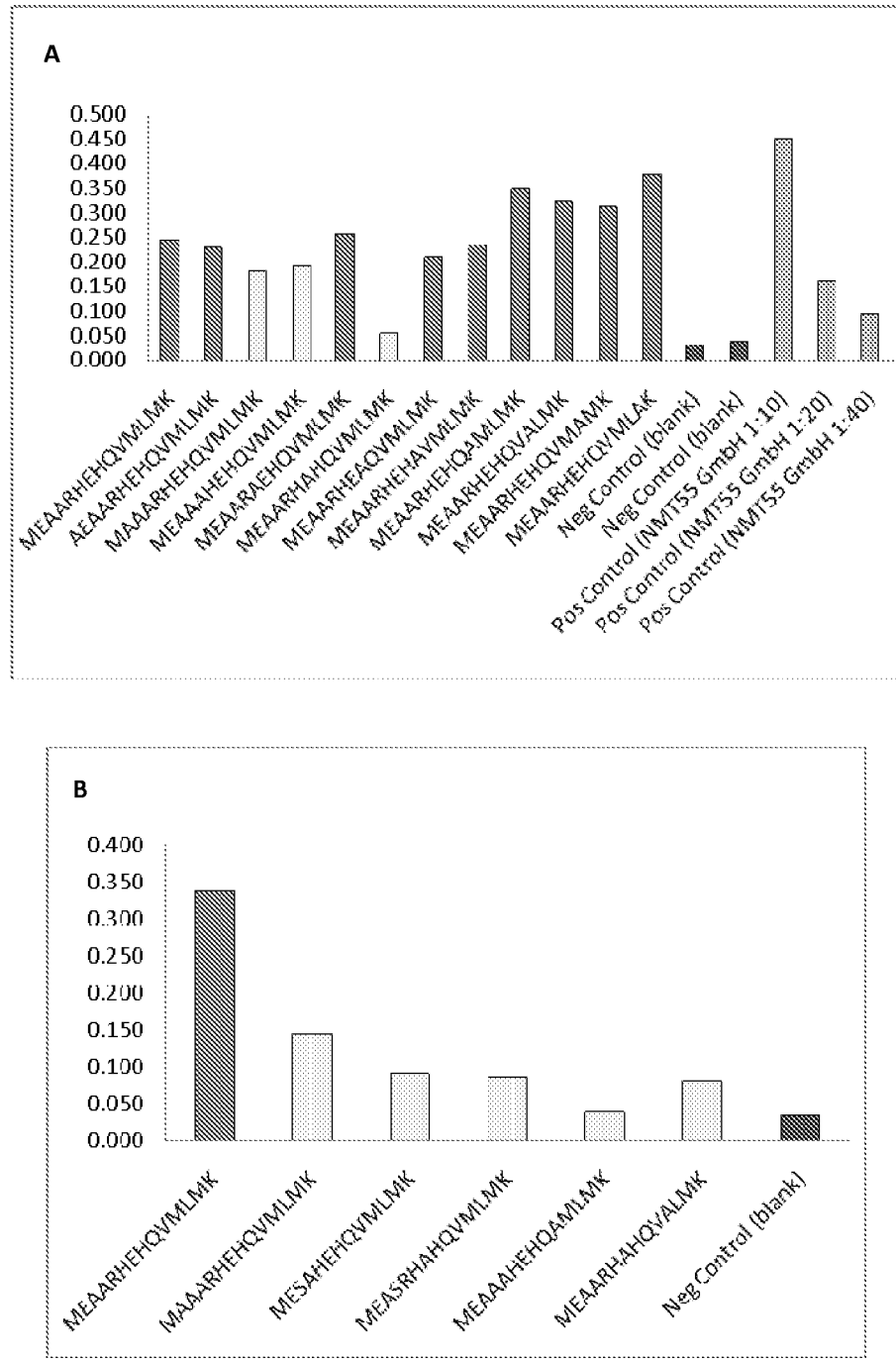
FIG. 4 shows ELISA results for binding of PAT-LM1 IgM to A) alanine substituted (from left to right, SEQ ID NOS:38-44, 47, 45, 46, 48 and 49) and B) serine substituted epitope sequences (from left to right, SEQ ID NOS: 38, 40, 50-53).

Alanine scanning experiments were then performed to map the minimal PAT-LM1 epitope on NMT55. A series of peptides with systematic alanine substitutions were synthesized. Equal amounts of peptides were coated on a Nunc plate and binding of PAT-LM1 IgM was tested by ELISA. The results are shown in FIG. 4A.

Another set of peptides that had alanine were substituted with serine and tested for PAT-LM1 IgM binding as outlined above, together with some of the alanine substituted peptides by ELISA. The results are shown in FIG. 4B.

From the alanine and serine scanning experiments it was concluded that the minimal PAT-LM1 epitope is EAARXE (SEQ ID NO: 3), wherein X can be any amino acid.

Example 2

Screening for Additional PAT-LM1 Epitopes (Mimotopes)

This example describes experiments utilising phage display libraries to screen for additional PAT-LM1 epitopes, or 'mimotopes'.
2.1 Materials and Methods
Dodecapeptide Phage Display Library Screening The Ph.D.12™ phage display peptide library kit was obtained from New England Biolabs, Inc. This is a combinatorial peptide 12-mer fused to the minor coat protein (pIII) of M13 phage. The displayed peptide 12-mers are expressed at the N terminus of pIII. The library consists of about $1.9 \times 10^9$ electroporated sequences, amplified once to yield about 20 copies of each sequence in 10 µl of the supplied phage.

Three biopannings were performed according to the manufacturer's instructions, with some modifications. For pre-clearing of the library, about 1 µg of an irrelevant human IgM (SAM6) was coupled to a 96 well polystyrene dish (Costar), blocked with about 0.1 M NaHCO$_3$ buffer (pH 8.6) containing about 5 mg/ml BSA and incubated for about 2 hours with about 10% library at room temperature (RT). This pre-absorbed supernatant (about 90 µl TBS/10 µl PH.D.-12) was used for first round of biopanning About 1 µg of PAT-LM1 (IgM) were coupled to a 96 well polystyrene dish and blocked with about 0.1 M NaHCO$_3$ buffer (pH 8.6) containing about 5 mg/ml BSA. Then, the dish was incubated for about 2 hours at RT with about 100 µl pre-absorbed supernatant and washed about six times with about 50 mM Tris and 150 mM NaCl (pH 7.5) containing about 0.5% Tween 20 (TBS/Tween). The bound phages were then eluted from the 96 well with about 100 µl of elution buffer (about 0.1 N HCl (pH adjusted to 2.2 with glycine) and about 1 mg/ml BSA) for 15 minutes. After neutralization with about 15 µl of about 1 M Tris-HCl (pH 9.1), the eluted phages were amplified by infection of about 20 ml of about a 1:100 dilution of an overnight culture of *E. coli* ER2537 (recA+ strain cells), as recommended by the manufacturer. The phages were incubated for about 4.5 hours at about 37° C. with vigorous shaking and purified by double precipitation in the cold with about ⅙ volume of polyethylene glycol (PEG)-NaCl (20% [vol/vol] polyethylene glycol 8000, 2.5 M NaCl).

In the second and third rounds of selection, about 10% of the amplified phages from the preceding round were preincubated for about 2 hours at RT with coated hIgM (PAT-LM1) at final concentrations of about 100 µg/ml. The procedure was then identical to the first round. Single phage clones from the third biopanning eluate were isolated and amplified for ELISA analysis and DNA sequencing.
Phage Binding ELISA Rows of ELISA plate wells were coated with about 100 µl of either PAT-LM1 (IgM) or SAM6 (IgM) or uncoated at a final concentration of about 100 µg/ml in about 0.1 m NaHCO$_3$ buffer (pH 8.6). The plates were incubated overnight at about 4° C. and then blocked with about 0.1 M NaHCO$_3$ buffer (pH 8.6) containing about 5 mg/ml BSA. After about 2 hours of incubation at RT, the plate was washed about six times with TBS/Tween. 8-fold serial dilutions of amplified eluate from biopanning 1-3 were added to each well of the microtiter plate in a final volume of about 100 μl of TBS/Tween, starting with eluate-dilution of about 10-5 in the first well of a row and ending with about 10-12 in the eighth well. The plates were incubated for about 2 hours at RT with agitation and then washed about six times with TBS/Tween as described above. The bound phages were detected in a sandwich assay using horseradish peroxidase-conjugated anti-M13 monoclonal antibody at about a 1:4000 dilution (GE healthcare). The plate was developed using a commercial color kit (BioRad) containing 3,3',5,5'-tetramethylbenzidine (TMB) and H$_2$O$_2$. After about 5 minutes of incubation and the reaction was stopped with about 50 μl 3N H$_2$SO$_4$ and the plate was read at about 450 nm with an ELISA plate reader.

Fluorescent Activated Cell Sorting (FACS)

Cells (A549, MKN-45 or HT-29 carcinoma cells) were grown to about 70-80% confluence and were detached with cell dissociation solution. The cell suspension was adjusted to about 2×10$^5$/ml in complete medium. Cells were placed on ice for about 30 minutes.

About 1 ml cell suspension was dispensed per FACS tube. Suspension was spun down with about 500 g at about 4° C. for about 5 minutes. Supernatant was discarded and cells were resolved in about 500 μl FACS Flow (Becton-Dickinson, 342003). Again suspension was spun down with about 500 g at about 4° C. for about 5 minutes and supernatant was discarded.

About 50 μg/ml human IgM in about 200 μl FACS Flow was added to the cells and incubated for 30 minutes on ice. For saturation of antibody, about 5 μg/ml PAT-LM1 "additional epitope 2" (SEQ ID NO 8) or about 5 μg/ml Sam-3 epitope were added to the antibody solution and preincubated for about 15 minutes. Sam-3 antibody was as represented by DSMZ Deposit No. DSM ACC3060. Same was done with isotype control (ChromPure (CP) IgM 009-000-012, dianova, 4.4 mg/ml, negative control: #1) and with buffer without first antibody (negative control: #2).

The suspension was spun down with about 500 g at about 4° C. for about 5 minutes and cells were washed with about 500 μl FACS Flow. Cells were resuspended in about 200 μl FACS Flow with about 1:50 dilution of secondary antibody (anti-human IgM-FITC, F(ab)2, DAKO F0317) and incubated at about 4° C. for about 30 minutes in the dark. Cells were washed two times with ice cold FACS Flow and resuspended in about 250 μl FACS Flow. Flourescence was measured with FACS Calibur, Becton-Dickinson (bandpass filter FITC: 530 nm).

2.2 Results

Two epitopes were identified through the above phage display experiments ("Epitope 1" and "Epitope 2"). These epitopes were then subjected to further fine mapping by systematically deleting one amino acid from either the N or C-terminus, as outlined in FIGS. 5A and 6A, respectively.

Figure 5:
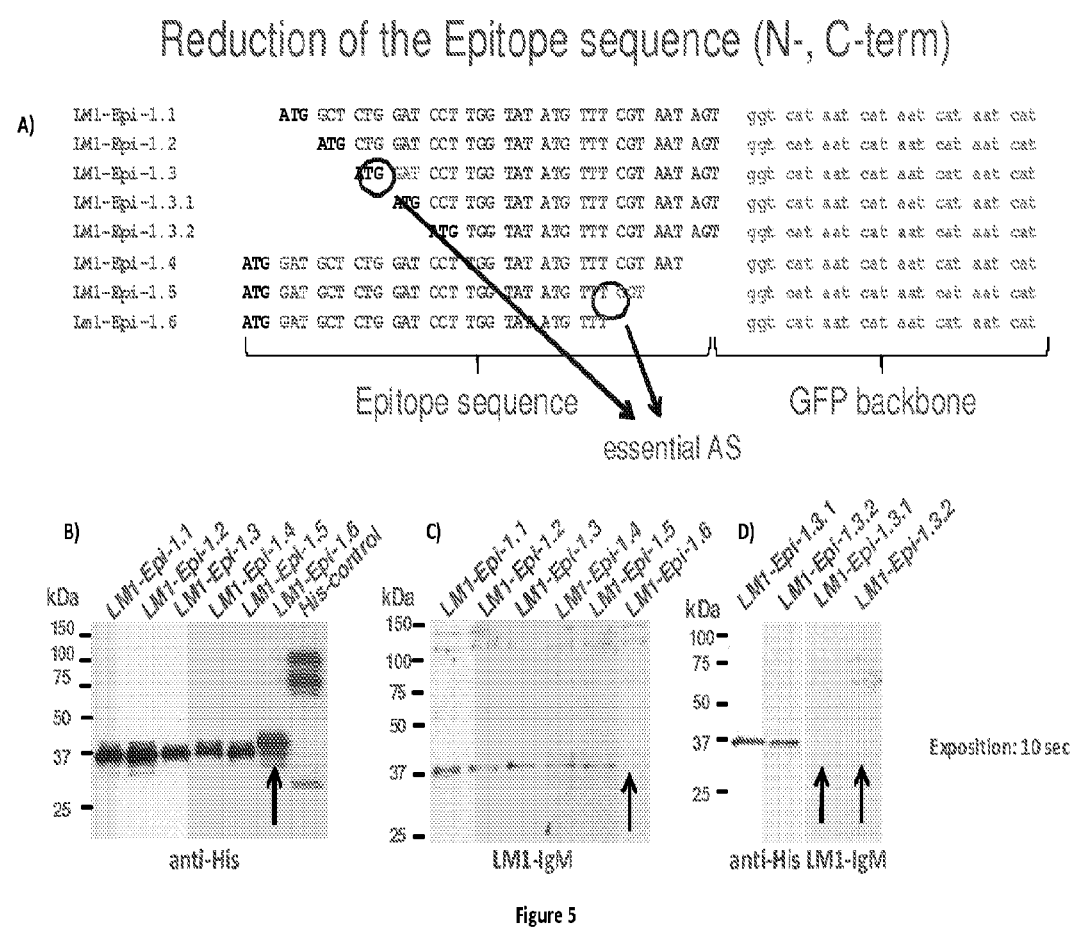

As can be seen in FIGS. 5A, C and D, PAT-LM1-Epi-1.1, PAT-LM1-Epi-1.2, PAT-LM1-Epi-1.3, PAT-LM1-Epi-1.4 and PAT-LM1-Epi-1.5 were the only polypeptides to show binding to PAT-LM1 antibody. PAT-LM1-Epi-1.3.1, PAT-LM1-Epi-1.3.2 and PAT-LM1-Epi-1.6 failed to show binding to PAT-LM1 antibody. Thus it was concluded that the minimal epitope for "Epitope 1" was DPWYMFR (SEQ ID NO: 4; "additional PAT-LM1 epitope 1").

Figure 6:
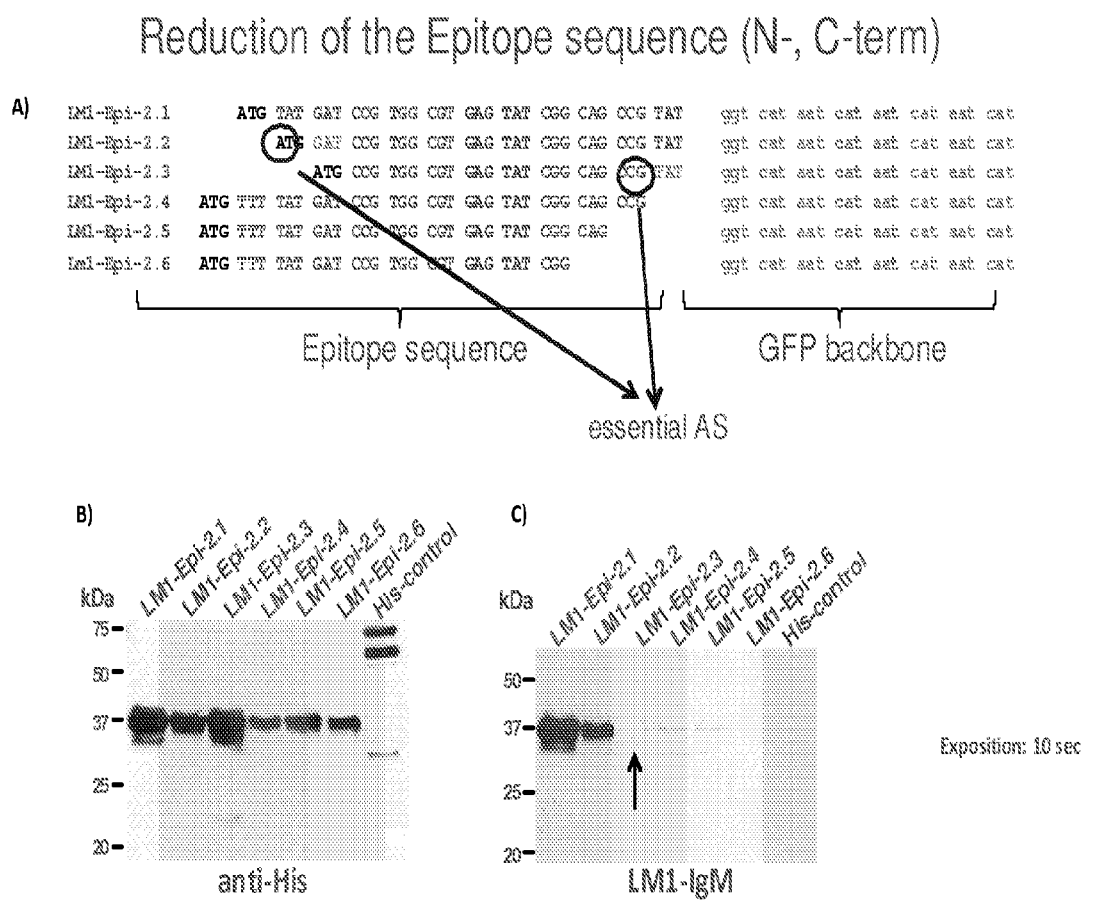

As can be seen in FIGS. 6A and C, PAT-LM1-Epi-2.1 and LM-Epi-2.2 were the only polypeptides to show binding to PAT-LM1 antibody. PAT-LM1-Epi-2.3, PAT-LM1-Epi-2.4, PAT-LM1-Epi-2.5 and PAT-LM1-Epi-2.6 failed to show binding to PAT-LM1 antibody. Thus it was concluded that the minimal epitope for "Epitope 2" was DPWREYRQPY (SEQ ID NO: 5; "additional PAT-LM1 epitope 2").

Figure 7:
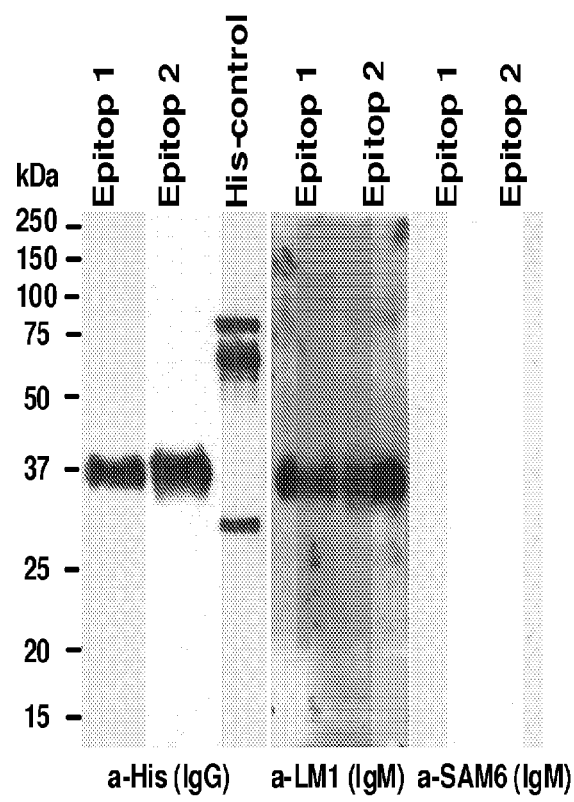
FIG. 7 shows a Western blot in which it was confirmed that PAT-LM1 antibody binds the minimal epitopes for "Epitope 1" and "Epitope 2".

Western blots were performed as described above and confirmed that PAT-LM1 antibody binds the minimal epitopes for "Epitope 1" and "Epitope 2" (see FIG. 7).

Figure 8:
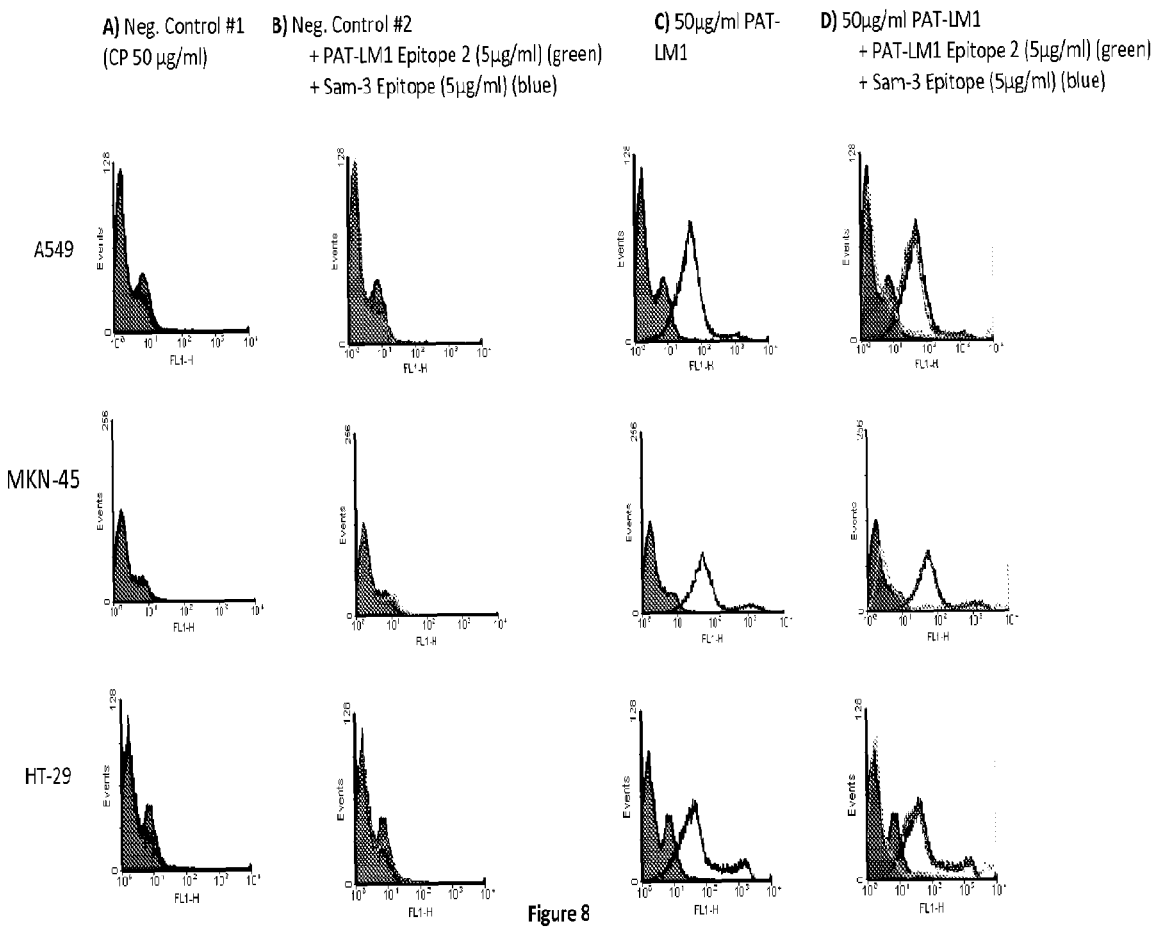
FIG. 8 shows fluorescent activated cell sorting (FACS) results for: A) Negative control #1 (Chrom Pure CP antibody alone); B) Negative control #2 (buffer plus PAT-LM1-epitope 2; green or Sam-3 epitope; blue); C) PAT-LM1 antibody alone; D) PAT-LM1 antibody plus PAT-LM1-epitope 2 (green) or Sam-3 epitope (blue). Binding of PAT-LM1 antibody to cells (C) is inhibited when PAT-LM1 antibody is preincubated with PAT-LM1 additional epitope 2 (SEQ ID NO: 8) (D).

The results from the fluorescent activated cell sorting (FACS) experiments are shown in FIG. 8. The results show that PAT-LM1 binding to cells (see FIG. 5C) is inhibited by preincubation of the antibody with "additional PAT-LM1 epitope 2" (SEQ ID NO: 5) (see FIG. 8D) isolated from the phage display library.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

REFERENCES

Altschul et al. (1990) Mol. Biol., 215 403
Ausubel et al. (2001) Current Protocols in Molecular Biology, Wiley literscience, New York
Beaucage et al. (1981) *Tetrahedron Letters*, 22:1859-1862
Borisova et al. (1999) *Vopr. Virusol.* 44:172-174
Bostick et al. (2003) *Biochem Biophys Res Commun.* 304:320
Bron et al. (1984) *Proc. Natl. Acad. Sci. USA*, 81:3214-3217
Bruggemann et al. (1987) *J. Exp. Med.* 166:1351-1361
Carpino and Han (1972) *J. Org. Chem.*, 37:3403-3409
Caruthers, M. H. et al. (1988), *Methods in Enzymology*, Vol. 154, pp. 287-314
Chappel et al. (1991) *Proc. Natl Acad. Sci. USA*, 88: 9036-9040
Coligan (1991) *Current Protocols in Immunology*, Wiley/Greene, NY
Delvig et al. (1995) *Hum. Antibodies Hybridomas*, 6:42-46
Elloington and Szostak (1990) *Nature*, 346:818-22
Encyclopedia of Pharmaceutical Technology, eds. J. Swarbrick and J. C. Boylan, 1988-1999, Marcel Dekker, NY
Gazzano-Santoro et al, (1996) *J. Immunol.* Methods 202: 163
Geysen et al. (1986) *Mol. Immunol.* 23:709-715
Goding (1986) Monoclonal Antibodies: Principles and Practice, 2d ed. Academic Press, NY
Harlow and Lane (1989) Antibodies: A Laboratory Manual, Cold Spring Harbor Press, NY
Harlow and Lane, (1999) Using Antibodies: A Laboratory Manual, Cold Spring Harbor Laboratory Press, N.Y.
Hellstrom et al., (1986) Proc. Natl Acad. Sci. USA 83:7059-7063
Hoogenboom (2005) Nature Biotechnol. 23:1105
Houghten, (1985) *Proc. Natl. Acad. Sci. USA* 82: 5131-5135
Huston et al. (1993) Cell Biophys. 22:189-224
Jones et al., (2010) *J Immunol Methods*, 354:85-90
Jostock et al. (2004) *J Immunol Methods*, 289: 65-80
Kabat et al., (1991) United States Public Health Service, National Institutes of Health, Bethesda 5$^{th}$ Ed.
Kanda et al. (2007) *J. Biotechnol*, 130: 300-310
Kennedy et al. (1976) *Clin. Chim.*, Acta 70, 1-31
Kerr et al., (1972) *Br. J. Cancer* 26: 239-257
Kohler and Milstein (1975) *Nature*, 256:495-497
Largaespada et al, (1996) *J. Immunol. Methods.*, 197: 85-95
Merrifield, (1963) *J. Am. Chem. Soc.*, 85:2149-2154
Messing (1983) *Methods Enzymol*, 101: 20-78
Mori et al. (2004) *Biotechnol. Bioengineer.*, 88: 901-908

Niman et al. (1983) *Proc. Natl. Acad. Sci. USA*, 80:4949-4951
Novotny et al. (1991) *Proc Natl Acad Sci USA*, 88:8646-8650
Olsnes and Pihl (1973) *Biochem.*, 12(16):3121-3126
Pearson et al. (1988) *Proc. Natl. Acad. Sci USA*, 85:2444
Pearson (2000) *Methods Mol Biol.*, 132:185
Remington (2000) *The Science and Practice of Pharmacy* (20th ed.), ed. A. R. Gennaro, Lippincott Williams & Wilkins
Runge et al. (1984) *Invest. Radiol.*, 19:408-415
Sambrook et al. (2001), *Molecular Cloning: A Laboratory Manual*, 3rd edition
Scopes (1982) *Protein Purification*, Springer-Verlag, NY
Schaefer et al. (1989) *JACC*, 14:472-480
Schurs et al. (1977) *Clin. Chim. Acta*, 81, 1-40
Shreve et al. (1986) *Magn. Reson. Med.*, 3:336-340
Smith et al. (1981) *J. Mol. Biol.*, 147:195
Stewart and Young (1984) *Solid Phase Peptide Synthesis*, 2 ed. Pierce, Rockford, Ill.
Stites et al. (1986) *Basic and Clinical Immunology*, 4th ed.
Umāna et al. (1999) *Nat. Biotechnol.*, 17: 176-180
Vollmers et al. (1994) *Cancer*, 74: 1525-1532
Vollmers et al. (1998) *Oncology Reports*, 5:35-40
Wesbey et al. (1984) *Physiol. Chem. Phys. Med. NMR*, 16:145-155
Wolf (1984) *Physiol. Chem. Phys. Med. NMR* 16:93-95
Wyllie et al. (1999) *Br. J. Cancer*, 80 Suppl. 1:34-37
Yumane-Ohnuki et al. (2004) *Biotechnol. Bioengineer*, 87: 614-622

The invention claimed is:

1. An isolated peptide consisting of an amino acid sequence shown in SEQ ID NO:3.

2. A composition comprising the peptide of claim 1 and an adjuvant.

3. A method of inducing an immune response in a subject comprising administering the peptide of claim 1 to said subject.

4. A method of inducing an immune response in a cancer subject comprising administering the peptide of claim 1 to said subject.

5. A method for assaying, enriching, isolating or purifying at least one antibody or antigen binding fragment thereof which comprises contacting the antibody or antigen binding fragment thereof with the peptide of claim 1.

* * * * *